United States Patent
Tomoda et al.

(10) Patent No.: US 10,672,121 B2
(45) Date of Patent: Jun. 2, 2020

(54) ANALYSIS METHOD AND ANALYZER

(71) Applicant: Sysmex Corporation, Kobe-shi, Hyogo (JP)

(72) Inventors: Sayuri Tomoda, Kobe (JP); Nobuhiro Kitagawa, Kobe (JP); Jianyin Lu, Kobe (JP); Kosuke Jitsuhara, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 15/608,288

(22) Filed: May 30, 2017

(65) Prior Publication Data

US 2017/0345148 A1    Nov. 30, 2017

(30) Foreign Application Priority Data

May 31, 2016    (JP) .................... 2016-109627

(51) Int. Cl.
| | |
|---|---|
| *G01N 21/64* | (2006.01) |
| *G01N 21/00* | (2006.01) |
| *G01N 33/543* | (2006.01) |
| *G01N 35/00* | (2006.01) |
| *G06T 7/00* | (2017.01) |
| *G01B 11/24* | (2006.01) |
| *G01N 21/03* | (2006.01) |
| *G01V 8/10* | (2006.01) |
| *H04N 7/18* | (2006.01) |
| *G01N 21/76* | (2006.01) |

(52) U.S. Cl.
CPC ............ *G06T 7/0012* (2013.01); *G01B 11/24* (2013.01); *G01N 21/03* (2013.01); *G01N 21/6428* (2013.01); *G01N 21/6452* (2013.01); *G01N 33/54326* (2013.01); *G01N 33/54366* (2013.01); *G01N 35/00069* (2013.01); *G01N 35/00871* (2013.01); *G01V 8/10* (2013.01); *H04N 7/183* (2013.01); *G01N 21/645* (2013.01); *G01N 21/76* (2013.01); *G01N 2021/6439* (2013.01); *G01N 2035/00158* (2013.01); *G01N 2201/062* (2013.01)

(58) Field of Classification Search
None
See application file for complete search history.

(56) References Cited

U.S. PATENT DOCUMENTS

| | | | |
|---|---|---|---|
| 2007/0081163 A1* | 4/2007 | Liang | G01N 21/253 356/445 |
| 2012/0092650 A1* | 4/2012 | Gunn, III | G01N 21/7746 356/73 |

(Continued)

FOREIGN PATENT DOCUMENTS

JP    2006-343335 A    12/2006

*Primary Examiner* — Neil N Turk
(74) *Attorney, Agent, or Firm* — Brinks Gilson & Lione

(57) ABSTRACT

Disclosed is an analysis method for detecting and analyzing light from a sample prepared so as to emit light in accordance with an amount of a test substance, the analysis method including taking an image of a storage member configured to store the sample therein; switching a state of a reflector to a state in which light from the sample is reflected toward a light detection unit and detecting light from the sample by the light detection unit; and outputting an analysis result of the sample on the basis of a light amount detected by the light detection unit.

20 Claims, 12 Drawing Sheets

(56) References Cited

U.S. PATENT DOCUMENTS

2013/0206701 A1    8/2013  Strohmeier et al.
2014/0308679 A1*  10/2014  Thompson ......... G01N 21/6428
                                                                   435/7.4

* cited by examiner

ANALYSIS METHOD AND ANALYZER

RELATED APPLICATIONS

This application claims priority from prior Japanese Patent Application No. 2016-109627, filed on May 31, 2016, entitled "ANALYSIS METHOD AND ANALYZER", the entire content of which is incorporated herein by reference.

BACKGROUND OF THE INVENTION

1. Field of the Invention

There are analyzers that perform analysis by detecting light from a sample (for example, see Japanese Laid-Open Patent Publication No. 2006-343335). There are also analyzers that perform specimen analysis by moving magnetic particles by means of a magnet (for example, see US Patent Application Publication No. 2013/0206701).

2. Description of the Related Art

Japanese Laid-Open Patent Publication No. 2006-343335 discloses an analyzer provided with a sensor structure serving as a storage member in which a luminescent sample is disposed; a detector which detects light from the luminescent sample; and a reflector which reflects, toward the detector side, light advancing from the sensor structure toward the side opposite to the detector. The reflector is disposed so as to cover the sensor structure. In Japanese Laid-Open Patent Publication No. 2006-343335, the light advancing from the sensor structure toward the side opposite to the detector can also be reflected by the reflector, to be detected by the detector. Thus, the detection sensitivity can be enhanced.

US Patent Application Publication No. 2013/0206701 discloses an analyzer provided with a magnet unit which moves magnetic particles in a disk.

The technology disclosed in Japanese Laid-Open Patent Publication No. 2006-343335 is a technology in which light released from the sensor structure to the outside is reflected by the reflector, thereby to collect light at the detector. However, there are cases where light released from the sensor structure to the outside is not sufficient, and thus, even when the light is reflected by the reflector, sufficient detection is not realized by the detector.

In particular, in a process that uses the technology disclosed in US Patent Application Publication No. 2013/0206701, a test substance bound to magnetic particles is transferred, an immune complex generated by causing the test substance to react with a labeled antibody is transferred, and a substrate is added to a sample including the immune complex, thereby causing light to be emitted. With regard to this process, unfavorable states are sometimes observed such as the sample is not appropriately transferred to a vessel where light caused by the addition of the substrate is to be detected; bubbles are mixed in the vessel; and magnetic particles are aggregated in the vessel. In such cases, light is not sufficiently released.

The present invention is directed to enabling confirmation of whether a sample serving as a light detection target is in an appropriate state, while enhancing the detection sensitivity of light from the sample.

SUMMARY OF THE INVENTION

The scope of the present invention is defined solely by the appended claims, and is not affected to any degree by the statements within this summary.

An analysis method according to a first aspect of the present invention is an analysis method for detecting and analyzing light from a sample prepared so as to emit light in accordance with an amount of a test substance, the analysis method including taking an image of a storage member configured to store the sample therein; switching a state of a reflector to a state in which light from the sample is reflected toward a light detection unit and detecting light from the sample by the light detection unit; and outputting an analysis result of the sample on the basis of a light amount detected by the light detection unit.

An analyzer according to a second aspect of the present invention includes a holder configured to hold a storage member configured to store therein a sample prepared so as to emit light in accordance with an amount of a test substance; a light detection unit configured to detect light from the sample stored in the storage member held by the holder; an imaging unit configured to take an image of the storage member; and a reflector configured to be switchable between a first state in which light advancing from the sample toward the imaging unit is reflected toward the light detection unit, and a second state in which light advancing from the storage member toward the imaging unit is not hindered.

DETAILED DESCRIPTION OF THE PREFERRED EMBODIMENTS

Hereinafter, embodiments are described with reference to the drawings.

Overview of Analyzer

With reference to FIG. 1, an overview of an analyzer according to the present embodiment is described.

An analyzer 100 according to the present embodiment is an apparatus configured to perform analysis by holding a storage member which stores therein a sample prepared so as to emit light in accordance with the amount of a test substance, and by detecting light released from the sample.

A sample 10 is a luminescent sample that is prepared so as to emit light in accordance with the amount of a test substance. The sample 10 generates light in the form of chemiluminescence or fluorescence, for example. The sample 10 may be a sample prepared by allowing a test substance to bind to a labeled substance, for example.

A test substance is one or more of antigens, antibodies, or other proteins, for example. A labeled substance is a substance that specifically binds to the test substance and that contains a label for causing light to be generated. The label is an enzyme, a fluorescent substance, or the like. Examples of the enzyme include alkaline phosphatase (ALP), peroxidase, glucose oxidase, tyrosinase, and acid phosphatase. As the fluorescent substance, fluorescein isothiocyanate (FITC), green fluorescent protein (GFP), luciferin, or the like can be used.

When the labeled substance contains an enzyme, the substrate for the enzyme of the labeled substance may be selected from a known substrate as appropriate according to the enzyme. When the enzyme is alkaline phosphatase, examples of the substrate include chemiluminescent substrates such as CDP-Star (registered-trademark), (disodium 4-chloro-3-(methoxyspiro[1,2-dioxetane-3,2'-(5'-chloro)tricyclo[3.3.1.13,7]decane]-4-yl)phenylphosphate), and CSPD (registered-trademark) (disodium 3-(4-methoxyspiro[1,2-dioxetane-3,2-(5'-chloro)tricyclo[3.3.1.13,7]decane]-4-yl) phenylphosphate); luminescent substrates such as p-nitrophenyl phosphate, 5-bromo-4-chloro-3-indolyl phosphate (BCIP), 4-nitro blue tetrazolium chloride (NBT), and iodonitrotetrazolium (INT); fluorescent substrates such as 4-methylumbelliferyl phosphate (4MUP); chromogenic substrates such as 5-bromo-4-chloro-3-indolyl phosphate (BCIP), disodium 5-bromo-6-chloro-indolyl phosphate, and p-nitrophenyl phosphate; and the like.

Figure 2A:
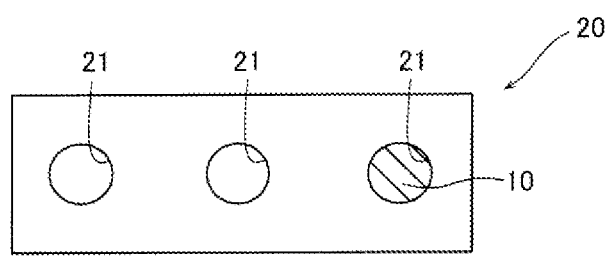
FIG. 2A shows a configuration example of a storage member.

A storage member 20 is a member in which a sample 10 is stored for light detection. The storage member 20 can receive the sample 10 and hold the sample 10 while the detection is performed. The storage member 20 is a disposable sample container for storing the sample 10, for example. The storage member 20 may be, for example, a cuvette for storing the sample 10, a plate (see FIG. 2A) having formed therein a well 21 for receiving the sample 10, or the like. A prepared sample 10 is placed in the storage member 20, but other than this, a process for preparing a sample 10 may be performed in the storage member 20. In such a case, the analyzer 100 may perform part or all of the process for preparing a sample 10.

Figure 2B:
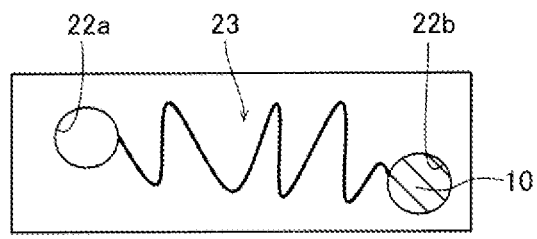
FIG. 2B shows a configuration example of the storage member.

In a case where the process for preparing a sample 10 is performed in the storage member 20, the storage member 20 may be, for example, a cartridge (see FIG. 2B) for preparing a sample by receiving a specimen that contains a test substance and mixing the specimen with a reagent. The cartridge may be a μ-TAS (Micro-Total Analysis System) chip having formed therein a micro flow path for causing a test substance to be moved, for example. In such a case, the storage member 20 (see FIG. 2B) includes a portion 22a for receiving a specimen that contains a test substance; a portion 22b for storing a prepared sample 10; a passage 23 for transferring the specimen from the portion 22a to the portion 22b during a preparation process; and the like.

As shown in FIG. 1, the analyzer 100 includes a holder 30, a light detection unit 40, an imaging unit 50, and a reflector 60.

The holder 30 holds the storage member 20 in which a sample 10 is placed. In the configuration example shown in FIG. 1, the holder 30 holds the storage member 20 by gripping both lateral faces of the storage member 20. Other than this, for example, the holder 30 may be configured to support, from below, the storage member 20 placed on the upper face of the holder 30. For example, the holder 30 may be configured to hold the storage member 20 inserted in a recess having a shape that corresponds to the storage member 20. In a case where the storage member 20 is a plate or a cartridge having a plate shape, the storage member 20 is inserted or set inside the analyzer 100, whereby the storage member 20 is held by the holder 30 so as to be detachable from the analyzer 100. The holder 30 holds the storage member 20 at a predetermined position 101, for example.

The light detection unit 40 is configured to detect light from a sample 10 stored in the storage member 20 held by the holder 30. In a state where the storage member 20 is held by the holder 30, the sample 10 in the storage member 20 is located at the predetermined position 101. The light detection unit 40 is disposed at a predetermined light-receiving position 102 at which the light detection unit 40 can receive light generated from the sample 10 at the predetermined position 101. Of the light generated from the sample 10, light that has reached the light-receiving position 102 is detected by the light detection unit 40. The light detection unit 40 is implemented by a light sensor. The light sensor is, for example, a photomultiplier, a phototube, a photodiode, or the like.

The imaging unit 50 is configured to take an image of the sample 10 stored in the storage member 20 held by the holder 30. In a state where the storage member 20 is held by the holder 30, the imaging unit 50 can take images of the sample 10 stored in the storage member 20. The taken images of the sample 10 allow confirmation of the state inside the storage member 20.

The state inside the storage member 20 represents the state of the sample 10 relevant to the analysis accuracy, for example. Whether the sample 10 is disposed at an appropriate position, whether the amount of the sample 10 is appropriate, whether the color, etc., of the sample 10 is appropriate, and the like can be confirmed on the basis of the taken images. In a case where the storage member 20 is configured such that a sample can be transferred therein, whether the sample 10 has been appropriately transferred to a detection vessel for performing light detection can be confirmed on the basis of the taken images. On the basis of the taken images of the sample 10, the reliability of the detection result obtained by the light detection unit 40 may be evaluated.

The imaging unit 50 is implemented by, for example, a camera capable of taking still images, a video camera capable of taking moving images, or the like. The imaging unit 50 can take, at a predetermined imaging position 103 at least, an image of the sample 10 in the storage member 20 disposed at the predetermined position 101. The imaging unit 50 may be able to take an image of a position other than the predetermined position 101. In a case where the storage member 20 is configured such that a sample can be transferred therein, the imaging unit 50 may be configured so as to be able to take an image of a desired portion of the storage member 20 in association with the transfer of the sample. Therefore, the imaging unit 50 may be fixed in the analyzer 100, but may be provided so as to be movable in the analyzer 100. For example, in the configuration example shown in FIG. 1, the imaging unit 50 is fixed at a position opposed to the storage member 20 held by the holder 30. In the configuration example shown in FIG. 1, the imaging unit 50 is fixedly set at the imaging position 103 opposed to the storage member 20, and can take an image of the sample 10 stored in the storage member 20.

The reflector 60 is disposed to the side opposite to the light detection unit 40 relative to the storage member 20. The reflector 60 is disposed on the optical path of light that reaches the imaging unit 50 at the time when the imaging unit 50 takes an image of the sample 10. The reflector 60 can reflect light. In the present embodiment, the reflector 60 is configured to be able to be switched between a reflecting state P1 and a non-reflecting state P2.

Figure 1A:
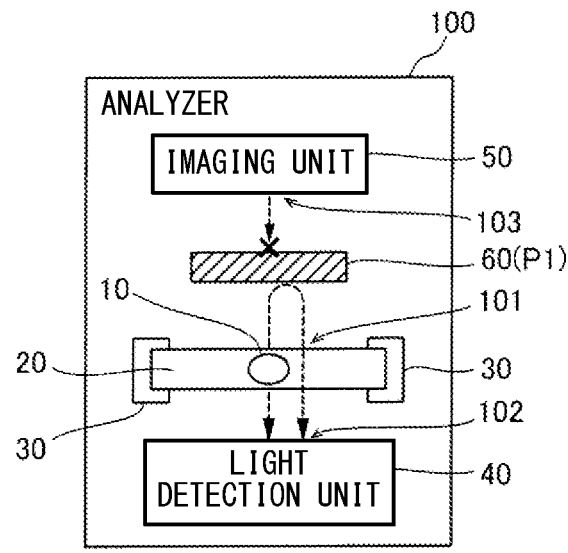
FIG. 1A is a schematic diagram of an analyzer in which a reflector is in a reflecting state.

As shown in FIG. 1A, the reflecting state P1 is a state in which light advancing from the storage member 20 held by the holder 30 toward the imaging unit 50 is reflected toward the light detection unit 40, thereby preventing the imaging unit 50 from taking an image of the sample 10. When the reflector 60 is in the reflecting state P1, the imaging unit 50 cannot take an image of the sample 10 at the predetermined position 101. In the reflecting state P1, light advancing from the sample 10 at the predetermined position 101 toward the reflector 60 is reflected toward the light-receiving position 102 where the light detection unit 40 is present. Thus, in the reflecting state P1, not only the light advancing from the sample 10 toward the light detection unit 40 but also the light reflected by the reflector 60 and advancing toward the light detection unit 40 are detected by the light detection unit 40. In order to allow the reflected light to easily reach the light detection unit 40, the portion, of the storage member 20, where the sample 10 is disposed has translucency.

Figure 1B:
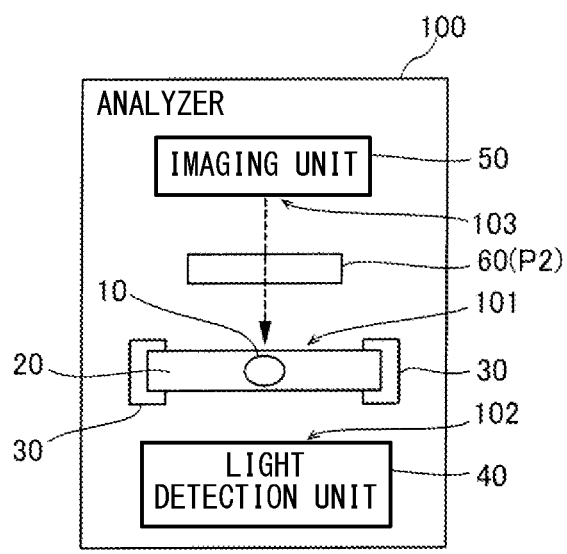
FIG. 1B is a schematic diagram of the analyzer in which the reflector is in a non-reflecting state.

As shown in FIG. 1B, the non-reflecting state P2 is a state in which light advancing from the storage member 20 held by the holder 30 toward the imaging unit 50 is not reflected, thereby not preventing the imaging unit 50 from taking an image of the sample 10. When the reflector 60 is in the non-reflecting state P2, the imaging unit 50 can take an image of the sample 10 at the predetermined position 101.

The reflector 60 is implemented by, for example, a mirror which reflects light. Switching between the reflecting state P1 and the non-reflecting state P2 is realized by the reflector 60 being moved, for example. The reflector 60 may be manually moved by a user, but the reflector 60 may be automatically moved. The imaging unit 50, the storage member 20, and the light detection unit 40 may be moved relative to the reflector 60. The reflector 60 may be implemented by a so-called light controllable mirror device or the like that can be electrically switched between a state in which light is reflected and a state in which light is allowed to be transmitted therethrough. In this case, relative movement between the reflector 60 and the imaging unit 50, the storage member 20, and the light detection unit 40 is not necessary.

Next, an analysis method performed by the analyzer 100 is described.

The analyzer 100 performs analysis by detecting light from a sample 10 stored in the storage member 20. In addition, the analyzer 100 takes images of the sample 10 stored in the storage member 20.

In a case where an image of a sample 10 is to be taken, the imaging unit 50 takes, from the imaging position 103, an image of the sample 10 at the predetermined position 101 in a state where the reflector 60 is switched at the non-reflecting state P2.

In a case where light from the sample 10 is to be detected, the light detection unit 40 detects light that has reached the light-receiving position 102, in a state where the reflector 60 is switched at the reflecting state P1. The light detection unit 40 outputs an electric signal according to a received light amount which is the amount of light detected by the light detection unit 40. Through analysis of the obtained electric signal, the presence/absence or the content of a predetermined component included in the sample 10 can be obtained, for example.

According to the configuration example shown in FIG. 1, the light detection unit 40 can detect light from the sample 10 in a state where the reflector 60 is switched at the reflecting state P1. Thus, the received light amount of the light detection unit 40 can be increased by an amount corresponding to the reflected light which is reflected by the reflector 60 and which is to be detected by the light detection unit 40. As a result, the detection sensitivity of light from the sample 10 can be enhanced. Since the reflector 60 can be switched to the non-reflecting state P2, the imaging unit 50 can take an image of the sample 10 stored in the storage member 20, even in a configuration where the reflector 60 is provided. As a result of these, while the detection sensitivity of light from the sample 10 is enhanced, the state inside the storage member 20 can be confirmed as necessary.

Configuration Example of Analyzer

Figure 3:
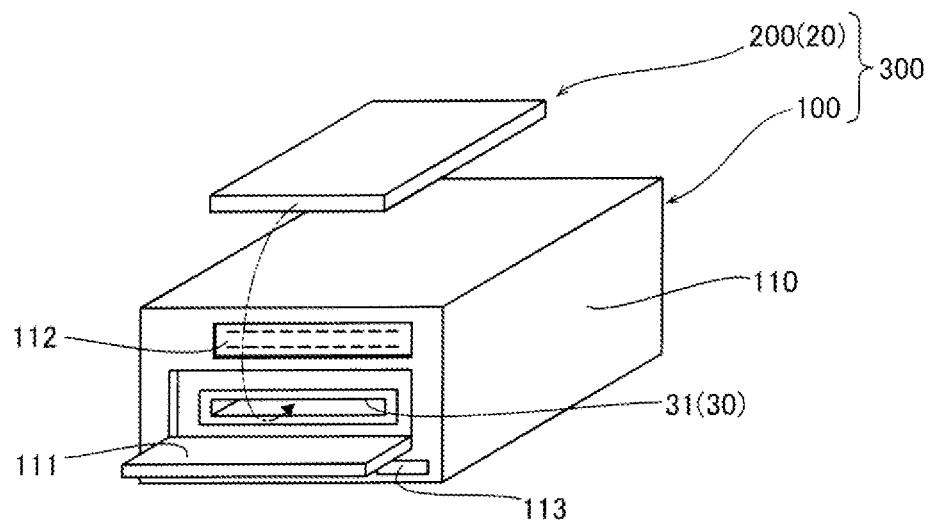
FIG. 3 is a schematic diagram showing a configuration example of the analyzer in which a cartridge is used.

FIG. 3 is an external view showing one configuration example of the analyzer 100. On the basis of the detected amount of light from the sample 10, the analyzer 100 can determine the presence/absence of a test substance in the specimen or the concentration of the test substance in the specimen. The analyzer 100 is small, and has a size that allows the analyzer 100 to be set on a desk in an examination room where a doctor examines a patient, for example. In FIG. 3, the size of the analyzer 100 is, for example, about 150 cm$^2$ to 300 cm$^2$ in terms of the installation area. For example, the analyzer 100 has a slot through which a cartridge 200 is inserted, and the cartridge 200 inserted in the slot is set at the holder 30 in the analyzer 100. The analyzer 100 performs an analysis process on the cartridge 200 set at the holder 30. An analysis system 300 is formed by the cartridge 200 and the analyzer 100.

In the configuration example shown in FIG. 3, the analyzer 100 includes a housing 110 for housing the apparatus body. A lateral face of the housing 110 is provided with a lid 111 which can be opened/closed to an open position where the slot is exposed and to a close position where the slot is covered; a display part 112; and an indicator 113. The cartridge 200 is inserted into the slot with the lid 111 open, and the analysis process is performed with the lid 111 closed. The display part 112 is implemented by, for example, a liquid crystal monitor or the like, and can display predetermined information such as analysis results. The indicator 113 is implemented by a lamp such as a light-emitting diode, and can indicate the state of the analyzer 100 by means of the lighting state, the color, or the like.

The analyzer 100 is not limited to the one as illustrated. The analyzer 100 may be configured such that, for example, a lid that can be opened/closed is provided at the upper face of the housing 110; the storage member 20 such as the cartridge 200 is set at the holder 30 in the apparatus in a state where the lid is open; and an analysis process is performed in a state where the lid is closed.

Configuration Example of Cartridge

Figure 4:
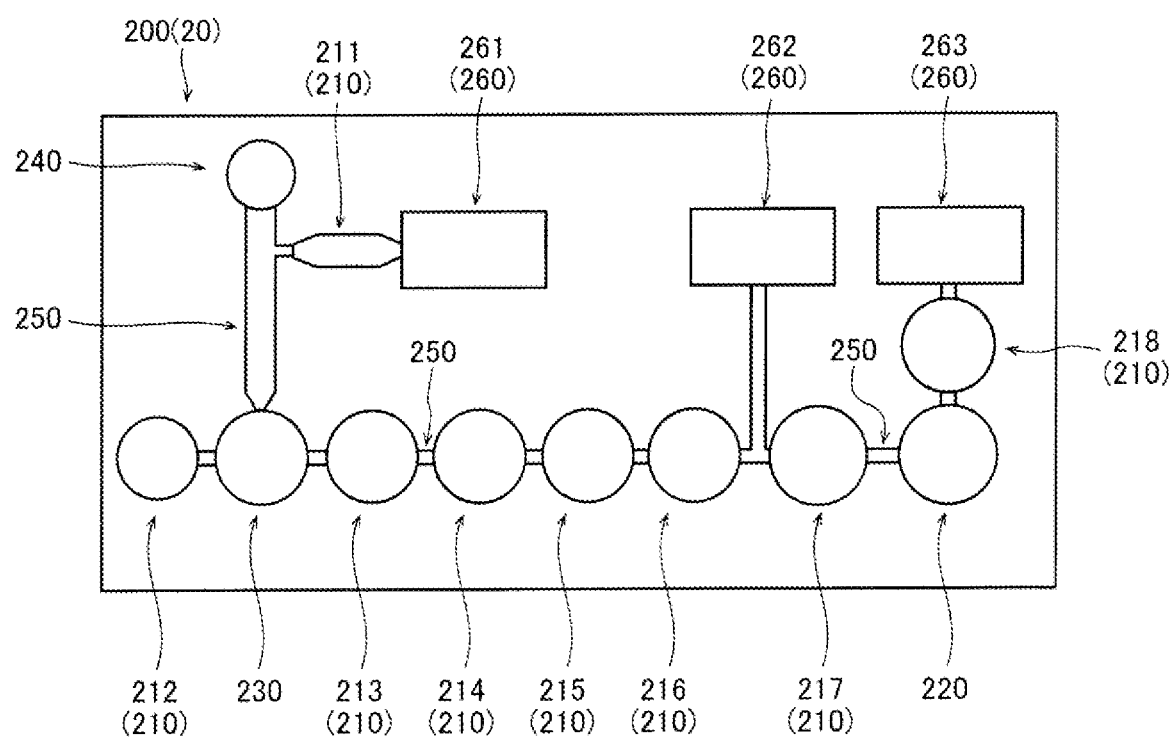
FIG. 4 is a plan view showing a configuration example of the cartridge.

FIG. 4 shows a specific configuration example of the cartridge 200 serving as the storage member 20 of the present embodiment. The cartridge 200 may be a disposable cartridge. In this case, the cartridge 200 is stored in a state of being kept in a package, and is used after being taken out of the package.

The cartridge 200 has a plurality of liquid storage portions 210 each for storing a liquid such as a specimen, a reagent, or a washing liquid. Here, an example in which the specimen is blood is shown. Some of the reagents include magnetic particles which react with a substance containing a test substance. The cartridge 200 has a detection vessel 220 and a liquid reaction portion 230.

The specimen is injected into a hemocyte separator 240 of the cartridge 200. A cartridge 200 with the hemocyte separator 240 sealed is inserted into the analyzer 100. The hemocyte separator 240 separates hemocyte components from the injected blood.

In the configuration example shown in FIG. 4, the liquid storage portions 210 include eight liquid storage portions 211 to 218. The liquid storage portions 211 to 218, the detection vessel 220, the liquid reaction portion 230, and the hemocyte separator 240 are arranged in the order according to process steps, and are connected via a passage portion 250 along the transfer route for liquid or magnetic particles.

The cartridge 200 has an air chamber 260. In the configuration example shown in FIG. 4, three air chambers 260, i.e., air chambers 261 to 263, are provided. Air sent out from the air chambers 260 causes a portion of the liquid in the cartridge 200 to be transferred.

Configuration Example of Analyzer

Figure 5:
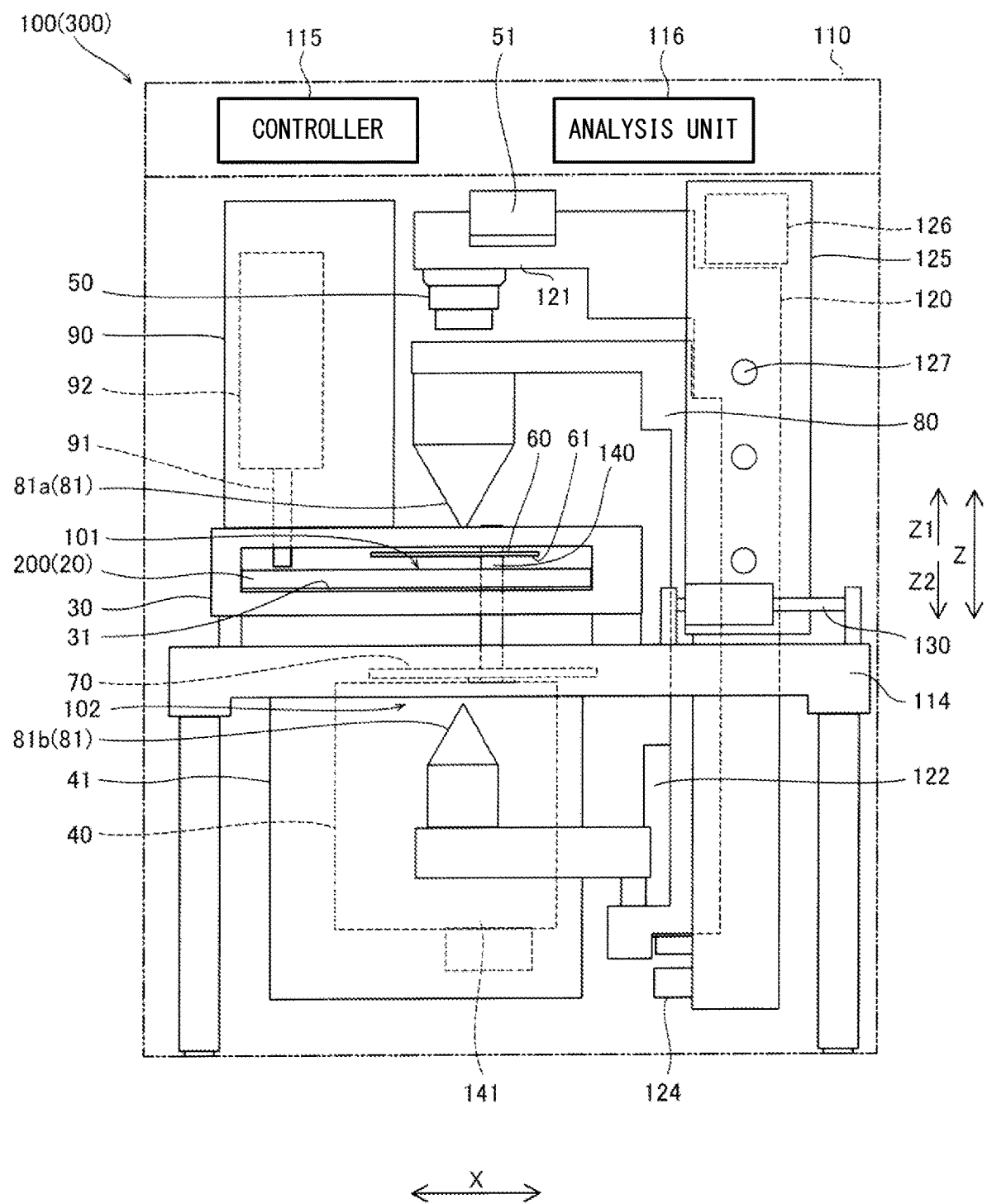
FIG. 5 is an internal front view showing a configuration example of the analyzer.
Figure 6:
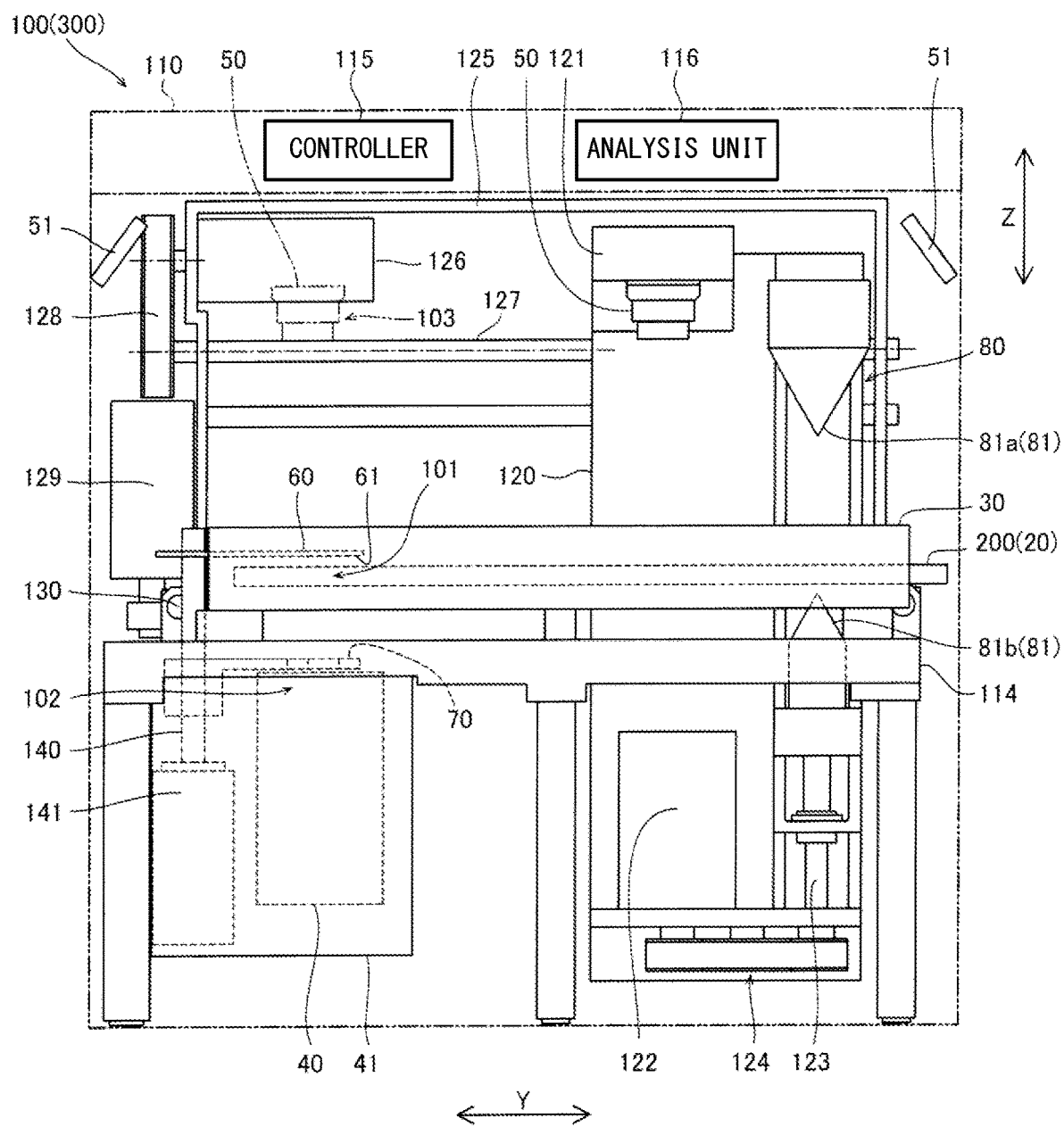
FIG. 6 is an internal side view showing a configuration example of the analyzer.
Figure 7:
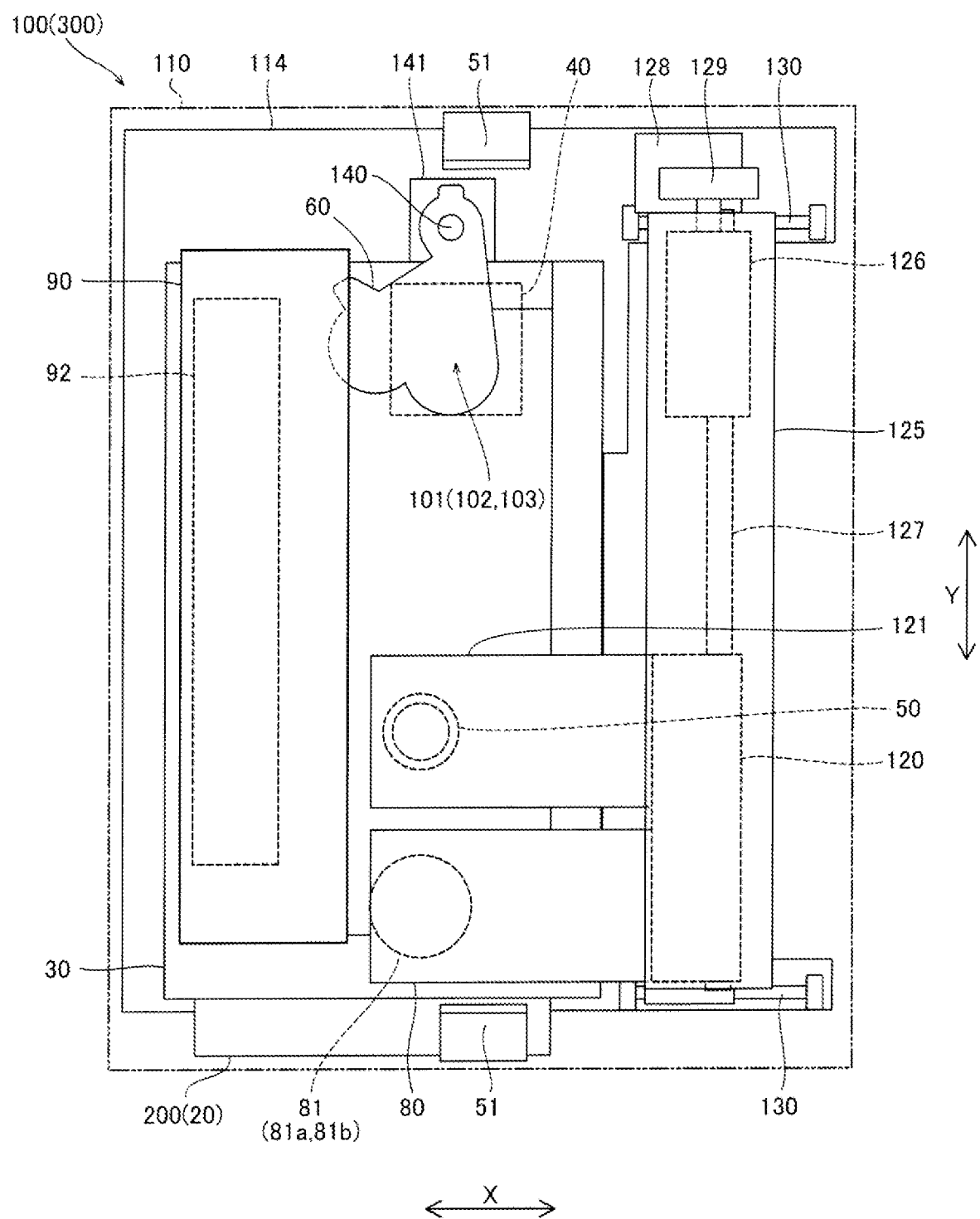
FIG. 7 is an internal plan view showing a configuration example of the analyzer.

FIG. 5 to FIG. 7 show specific configuration examples of the analyzer 100 in which the cartridge 200 is used as the storage member 20.

The analyzer 100 includes the holder 30, the light detection unit 40, the imaging unit 50, and the reflector 60. The holder 30, the light detection unit 40, the imaging unit 50, and the reflector 60 are housed in the housing 110. In the configuration example shown in FIG. 5 to FIG. 7, the analyzer 100 further includes a magnet unit 80 and a plunger unit 90.

The holder 30 holds, at the predetermined position 101, the cartridge 200 inserted through an opening 31 (see FIG. 5) which is a slot portion of the analyzer 100. The holder 30 holds the cartridge 200 in a state where the cartridge 200 is substantially parallel to the installation face of the analyzer 100. Since the installation face of the analyzer 100 can be regarded as being substantially horizontal, the face or the direction that is parallel to the installation face of the analyzer 100 is herein referred to as the horizontal plane or the horizontal direction. In the description below, for convenience, the short-side direction of the analyzer 100 in the horizontal plane is defined as X direction, and the longitudinal direction of the analyzer 100 in the horizontal plane is defined as Y direction. The up-down direction orthogonal to the X direction and the Y direction is defined as Z direction.

In the configuration example shown in FIG. 5 to FIG. 7, the holder 30 detachably holds the cartridge 200 which receives a test substance and which allows the test substance to be bound to a labeled substance, thereby preparing a sample 10. The holder 30 is configured to dispose, at the predetermined position 101 which allows the imaging unit 50 to take an image, the detection vessel 220 (see FIG. 4) storing the sample 10 therein of the storage member 20. This allows the analyzer 100 to perform preparation of a sample 10 and detection of light from the sample 10, in a state where the cartridge 200 having the specimen injected therein is set at the holder 30. Thus, there is no need to prepare a sample 10 in advance, and thus, convenience for the user is enhanced.

The holder 30 is set on a base 114 and can support the periphery of the cartridge 200. In order to allow taking images and light detection, the holder 30 is formed so as to partially expose the upper face and the lower face of the cartridge 200. The holder 30 may have any structure as long as the holder 30 can hold the cartridge 200.

The light detection unit 40 is fixedly disposed at the light-receiving position 102 below the predetermined position 101. The light detection unit 40 has the light-receiving position 102 at the upper face side which is the predetermined position 101 side. The light detection unit 40 detects, through an opening formed at the lower face side of the holder 30, light that has reached the light-receiving position 102 from the predetermined position 101. The light detection unit 40 is housed in a case 41, and is light-shielded except the light-receiving position 102.

In the configuration example shown in FIG. 5 to FIG. 7, the reflector 60 is a mirror member disposed at an upper position relative to the storage member 20 held by the holder 30 and to the side opposite to the light detection unit 40. The reflector 60 moves relative to the light detection unit 40, the storage member 20, and the imaging unit 50. The reflector 60 is configured such that the reflector 60 enters the reflecting state P1, between the storage member 20 and the imaging unit 50, and at a reflecting position which is opposed to the light detection unit 40 with the storage member 20 interposed between the light detection unit 40 and the reflector 60; and the reflector 60 enters the non-reflecting state P2 at a withdrawn position at which the reflector 60 does not block light advancing from the storage member 20 and reaching the imaging unit 50. Accordingly, simply by causing the reflector 60 to move relative to the light detection unit 40, the storage member 20, and the imaging unit 50, switching between the reflecting state P1 and the non-reflecting state P2 can be easily realized. Detailed configuration of the reflector 60 will be described later.

In the configuration example shown in FIG. 5 to FIG. 7, the analyzer 100 further includes a light adjuster 70 (see FIG. 5 and FIG. 6) disposed between the light detection unit 40 and the storage member 20 held by the holder 30. The light adjuster 70 is configured to be switchable between a light transmitting state in which light advancing from the storage member 20 toward the light detection unit 40 is allowed to be transmitted therethrough, and a light blocking state in which light advancing from the storage member 20 toward the light detection unit 40 is blocked. Accordingly, when light from a sample 10 is to be detected, light detection can be performed by setting the light adjuster 70 to the light transmitting state, and when detection is not performed, light onto the light detection unit 40 can be blocked by setting the light adjuster 70 to the light blocking state as necessary. Thus, unnecessary light from the outside can be suppressed from being incident on the light detection unit 40, and thus, the detection sensitivity of the light detection unit 40 can be further enhanced.

The imaging unit 50 is disposed above the cartridge 200 held by the holder 30. As shown in FIG. 5, the imaging unit 50 is provided at a position above the holder 30 such that the image taking direction thereof extends downward. The imaging unit 50 is configured to be movable in the X direction and in the Y direction. The imaging unit 50 can move in the horizontal direction in a range including the imaging position 103 at least.

As shown in FIG. 5 and FIG. 6, when the imaging unit 50 is located at the imaging position 103, the light detection unit 40 and the imaging unit 50 are disposed at positions opposed to each other with the storage member 20 interposed therebetween. The reflector 60 is disposed between the imaging unit 50 and the storage member 20, and has a reflection face 61 opposed to the light detection unit 40. This realizes a positional relationship in which the light detection unit 40, the imaging unit 50, and the storage member 20 are arranged on a straight line in the up-down direction. Therefore, a simple configuration can be employed in which the light reflector 60 having a flat-plate shape and having the reflection face 61 formed thereon is simply disposed between the imaging unit 50 and the storage member 20. Thus, even in a case where the reflector 60 switchable between the reflecting state and the non-reflecting state is provided, the configuration of the apparatus can be prevented from being complicated.

In order to allow taking images, the analyzer 100 includes a lighting unit 51. The lighting unit 51 is implemented by, for example, a light-emitting diode or the like. A pair of lighting units 51 is provided, for example, above the holder 30 and near both ends in the Y direction of the holder 30. Each lighting unit 51 is disposed near the center in the X direction, for example. Accordingly, the imaging field of the imaging unit 50 is illuminated by the illuminating light from both sides in the Y direction.

The magnet unit 80 includes a magnet 81. In the configuration example shown in FIG. 5, the magnet unit 80 has two magnets 81a and 81b. One magnet 81a is disposed above (Z1 side) the holder 30, and the other magnet 81b is disposed below (Z2 side) the holder 30. The magnet unit 80 holds the magnet 81a and the magnet 81b with a predetermined interval therebetween in the up-down direction. As shown in FIG. 6, the magnet unit 80 can move in each of the X direction, the Y direction and the Z direction. The imaging unit 50 can move in the X direction and in the Y direction, integrally with the magnet unit 80. The magnet unit 80 can move in the Z direction independently of the imaging unit 50. The imaging unit 50 does not move in the Z direction.

The magnet 81a and the magnet 81b each have a tapered shape, and the tip thereof serves as a magnetizing portion. The magnet 81a approaches the upper face of the cartridge 200 in association with movement of the magnet unit 80, whereby the magnet 81a causes magnetic force to act on the cartridge 200 from above. The magnet 81b approaches the lower face of the cartridge 200 in association with movement of the magnet unit 80, whereby the magnet 81b causes magnetic force to act on the cartridge 200 from below. In the holder 30, the upper face side and the lower face side of the cartridge 200 are exposed at least in the range in which the magnet 81a and the magnet 81b move.

The magnet unit 80 causes the magnet 81a or the magnet 81b to approach the cartridge 200, thereby collecting magnetic particles in the cartridge 200. The magnet unit 80 horizontally moves the magnet 81a or the magnet 81b located close to the cartridge 200, thereby moving the collected magnetic particles in the horizontal direction. The magnet unit 80 reciprocates in the up-down direction so that the magnet 81a and the magnet 81b alternately approach the cartridge 200, thereby being able to move the magnetic particles in the cartridge 200 in the up-down direction. As a result, the liquid in the cartridge 200 and the magnetic particles are stirred.

As shown in FIG. 5, the plunger unit 90 is disposed at the upper face side of the holder 30. The plunger unit 90 includes a plunger 91 and a drive unit 92 which operates the plunger 91. The plunger 91 is disposed above the air chambers 260 (see FIG. 4) of the cartridge 200 held in the holder 30, and can move in the up-down direction. The plunger 91 is provided by the same number as the air chambers 260, for example, and the drive unit 92 causes the respective plungers 91 to move in the up-down direction independently of or in conjunction with one another. The plunger unit 90 pushes down the air chambers 260 of the cartridge 200 by means of the plungers 91. Pushing down of the plungers 91 causes air to be sent out of the air chambers 260, whereby part or all of the liquid in the cartridge 200 is transferred. In the holder 30, the upper face side and the lower face side of the cartridge 200 are exposed at least in the range in which the magnet 81a and the magnet 81b move.

The analyzer 100 includes a controller 115 for controlling respective components of the apparatus, and an analysis unit 116 which analyzes an output signal from the light detection unit 40. The controller 115 controls the light detection unit 40, the imaging unit 50, and the reflector 60, thereby controlling image taking operation and light detecting operation. The analysis unit 116 performs analysis on the basis of the light amount detected by the light detection unit 40. The analyzer 100 may output the detection result of the light detection unit 40 to a computer that is separately provided, for example, and may perform analysis by use of the computer.

The controller 115 includes, for example, an arithmetic processor and a storage unit. The arithmetic processor is implemented by, for example, a CPU (central processing unit), an MPU (micro processing unit), or the like. The storage unit is implemented by, for example, a flash memory, a hard disk memory, or the like. The analysis unit 116 includes, for example, an arithmetic processor and a storage unit. The analysis unit 116 may be configured to function as the analysis unit 116 by the arithmetic processor of the controller 115 executing an analysis program stored in the storage unit. In this case, the controller 115 and the analysis unit 116 are configured as a common hardware. The controller 115 obtains a state of magnetic particles in a specimen cartridge 200, on the basis of data of an image taken by the imaging unit 50. The data of the image includes RGB pixel value information in each pixel of the image taken by the imaging unit 50. The controller 115 detects magnetic particles on the basis of contrast information or color information of the data of the image taken by the imaging unit 50.

Movement Mechanism for Imaging Unit and Magnet Unit

Movement mechanism for the imaging unit 50 and the magnet unit 80 in the configuration example shown in FIG. 5 to FIG. 7 is described. As shown in FIG. 6, the imaging unit 50 is fixed to an inner movable body 120. Specifically, the imaging unit 50 is mounted to a leading end portion of an arm 121 (see FIG. 5) extending in the X direction from an upper portion of the inner movable body 120. The magnet unit 80 is mounted so as to be movable in the up-down direction relative to the inner movable body 120. The inner movable body 120 is provided with a Z-axis motor 122 and a transmission mechanism. In FIG. 6, the transmission mechanism is configured by a combination of a feed-screw mechanism 123 extending in the Z direction and for moving the magnet unit 80; and a belt pulley mechanism 124 which transmits driving force of the Z-axis motor 122 to the feed-screw mechanism 123. Through rotation of the Z-axis motor 122, the magnet unit 80 moves in the Z direction relative to the inner movable body 120.

The inner movable body 120 is supported by an outer movable body 125 so as to be movable in the Y direction. The outer movable body 125 is provided with a Y-axis motor 126 and a transmission mechanism. In FIG. 6, the transmission mechanism is configured by a combination of a feed-screw mechanism 127 extending in the Y direction and for moving the inner movable body 120; and a belt pulley mechanism 128 which transmits driving force of the Y-axis motor 126 to the feed-screw mechanism 127. Through rotation of the Y-axis motor 126, the inner movable body 120 including the imaging unit 50 and the magnet unit 80 moves in the Y direction relative to the outer movable body 125.

The outer movable body 125 is supported by the base 114 so as to be movable in the X direction. An X-axis motor 129, a guide shaft 130 (see FIG. 7), and a transmission mechanism not shown are provided at the base 114. The guide shaft 130 guides movement in the X direction of the outer movable body 125. Through rotation of the X-axis motor 129, the outer movable body 125, and the inner movable body 120 including the imaging unit 50 and the magnet unit 80 move in the X direction relative to the base 114. The configurations of the transmission mechanisms and the motors are not limited to those shown. For example, the mechanism 124 which transmits the driving force of the Z-axis motor 122 and the mechanism which transmits the driving force of the Y-axis motor 126 may be implemented by gears.

Configuration of Reflector and Light Adjuster

With reference to FIG. 8 to FIG. 12, a configuration example of the reflector 60 and the light adjuster 70 is described.

Figure 8:
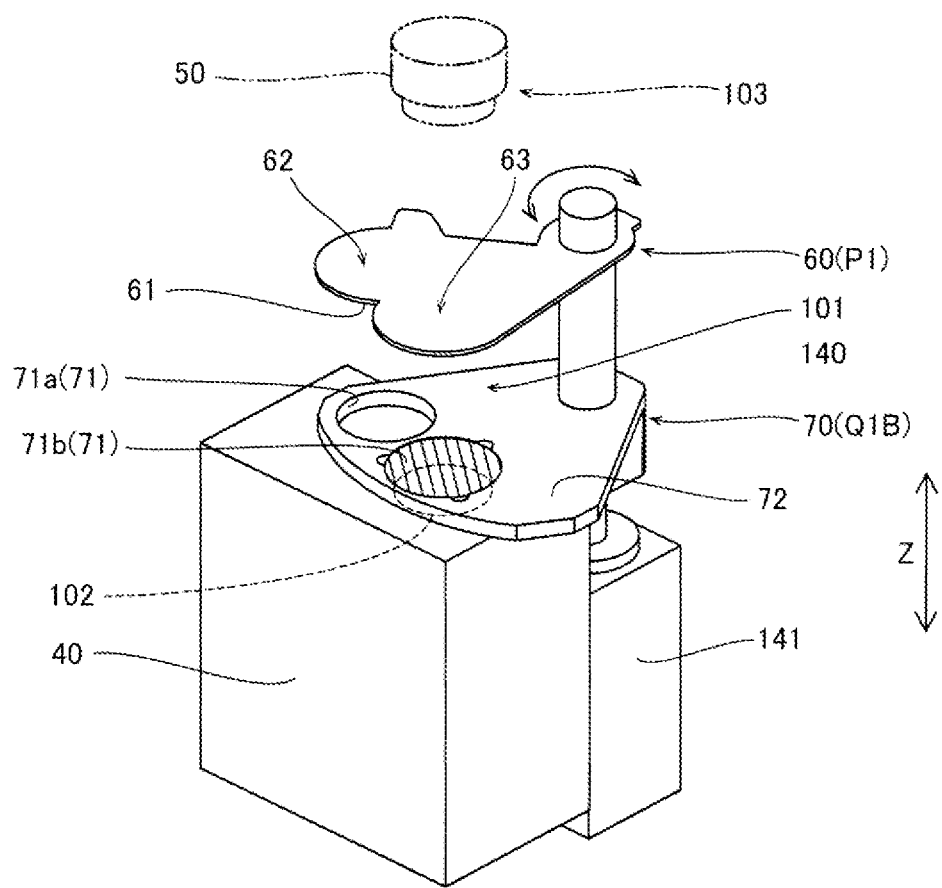
FIG. 8 is a perspective view showing a configuration example of the reflector and a light adjuster.
Figure 9:
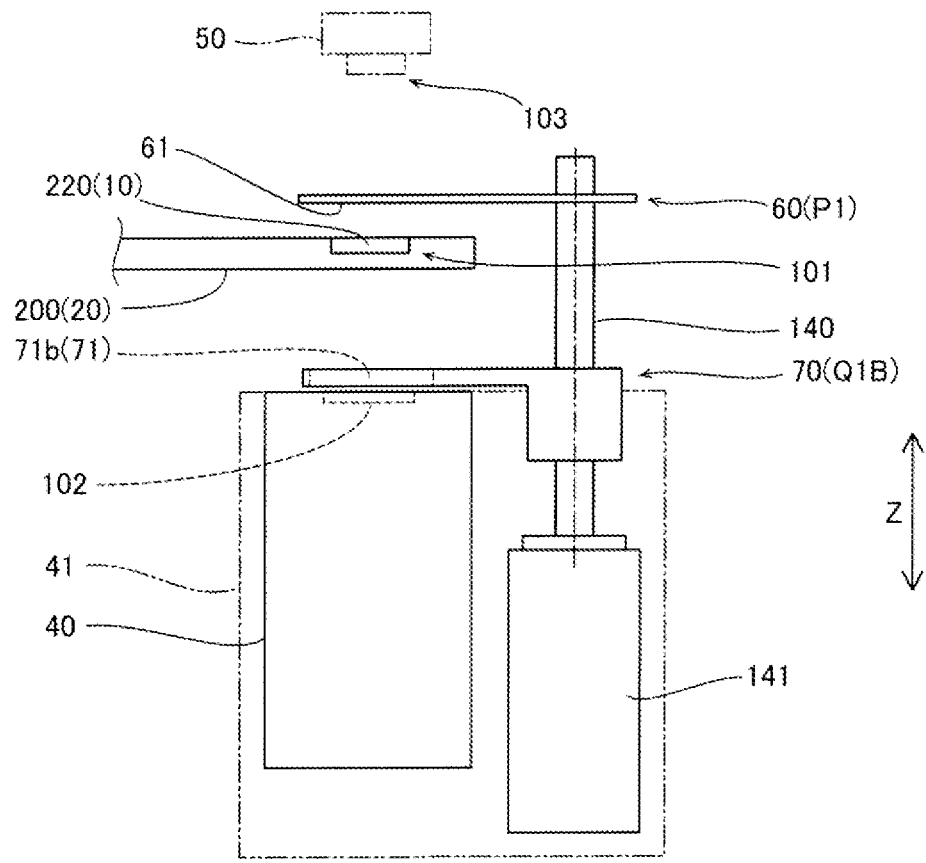
FIG. 9 is a side view showing a configuration example of the reflector and the light adjuster.

In the configuration example shown in FIG. 8 and FIG. 9, the reflector 60 is a plate-shaped member having the reflection face 61 on the lower face side thereof. The light adjuster 70 is a plate-shaped member that includes a light transmitting portion 71 which allows light to be transmitted therethrough; and a light blocking portion 72 which does not allow light to be transmitted therethrough.

The light adjuster 70 moves relative to the light detection unit 40, the storage member 20, and the imaging unit 50. The light adjuster 70 is switched to a light transmitting state Q1 (see FIG. 10, FIG. 11) by the light transmitting portion 71 being disposed between the light detection unit 40 and the storage member 20 held by the holder 30, and is switched to a light blocking state Q2 (see FIG. 12) by the light blocking portion 72 being disposed between the light detection unit 40 and the storage member 20. Thus, simply by causing the light adjuster 70 to move relative to the light detection unit 40, the storage member 20, and the imaging unit 50, switching between the light transmitting state Q1 and the light blocking state Q2 can be easily realized. In the configuration example shown in FIG. 8, the light adjuster 70 moves relative to the light detection unit 40, the storage member 20 and the imaging unit 50.

In the configuration example shown in FIG. 8, the reflector 60 and the light adjuster 70 are mounted to an identical rotation shaft 140, and associated with rotation of the rotation shaft 140, the state of the reflector 60 and the state of the light adjuster 70 are switched in conjunction with each other. Accordingly, simply by rotating the common rotation shaft 140, switching of the state of the reflector 60 and the switching of the state of the light adjuster 70 can be realized. Thus, the configuration of the apparatus can be simplified. Different from a case where switching of the state of the reflector 60 and switching of the state of the light adjuster 70 are individually performed, the state of the reflector 60 and the state of the light adjuster 70 can be reliably switched in conjunction with each other.

Specifically, as shown in FIG. 9, the rotation shaft 140 is provided so as to extend in the Z direction, and the lower end of the rotation shaft 140 is connected to a drive source 141. The drive source 141 is a stepping motor, for example. The drive source 141 causes the rotation shaft 140 to rotate about the central axis thereof extending in the Z direction. The reflector 60 is mounted to an upper portion of the rotation shaft 140, so as to be located at a position close to the upper side of the storage member 20 held by the holder 30. Accordingly, in the reflecting state P1, more of the light from a sample 10 can be reflected to the light detection unit 40 side. The light adjuster 70 is mounted to the rotation shaft 140, so as to be located at a position close to the upper side of the light-receiving position 102 of the light detection unit 40. Thus, in the light blocking state Q2, light can be more reliably suppressed from being incident on the light detection unit 40. The reflector 60 and the light adjuster 70 are fixed to the rotation shaft 140, and rotate integrally with the rotation shaft 140. The drive source 141 and a part of the rotation shaft 140 are housed in the case 41, together with the light detection unit 40.

In the configuration example shown in FIG. 8, the light adjuster 70 is configured to be switchable among a plurality of the light transmitting states Q1 in which light transmittances are different. Thus, the light adjuster 70 can be switched among three or more states including the light blocking state. This allows light transmittance to be switched in accordance with the amount of light generated from the sample 10. Thus, not only the detection sensitivity can be ensured when the light amount is small, but also saturation of the output from the light detection unit 40 can be suppressed even when the light amount is large.

In the configuration example shown in FIG. 8, the state of the light adjuster 70 includes a first light transmitting state Q1A (see FIG. 10) in which light advancing from the storage member 20 toward the light detection unit 40 is allowed to be transmitted through the through-hole 71a, and a second light transmitting state Q1B (see FIG. 11) in which light advancing from the storage member 20 toward the light detection unit 40 is allowed to be transmitted through a light reducing filter portion 71b. The reflector 60 is switched to the reflecting state P1 when the light adjuster 70 is in the first light transmitting state Q1A at least. Thus, when the amount of light generated from the sample 10 is small, the detectable light amount can be increased by the reflector 60 in the reflecting state P1, without reducing the light amount by the light adjuster 70 in the first light transmitting state Q1A. When the amount of light generated from the sample 10 is large, the light amount can be easily decreased by the light adjuster 70 in the second light transmitting state Q1B. As a result, the detection range of the light amount can be sufficiently ensured, while the detection sensitivity is enhanced.

In the configuration example shown in FIG. 8, the reflector 60 is switched to the reflecting state P1 when the light adjuster 70 is in the light transmitting state Q1. That is, not only in the case of the first light transmitting state Q1A (see FIG. 10) but also in the case of the second light transmitting state Q1B (see FIG. 11), the reflector 60 is set in the reflecting state P1.

In the configuration example shown in FIG. 8, the light adjuster 70 includes two light transmitting portions 71: the light transmitting portion 71 formed as the through-hole 71a; and the light transmitting portion 71 formed as the light reducing filter portion 71b. The light adjuster 70 includes the through-hole 71a, the light reducing filter portion 71b, and the light blocking portion 72. The through-hole 71a, the light reducing filter portion 71b, and the light blocking portion 72 have substantially equal distances in the radial direction from the rotation shaft 140, and are disposed at different positions in the rotation direction. These distances in the radial direction from the rotation shaft 140 are substantially equal to the distance from the rotation shaft 140 to the light-receiving position 102 of the light detection unit 40.

Thus, in accordance with the rotation angle of the rotation shaft 140, the light adjuster 70 is switched among the first light transmitting state Q1A (see FIG. 10) in which the through-hole 71a is disposed between the light detection unit 40 and the storage member 20; the second light transmitting state Q1B (see FIG. 11) in which the light reducing filter portion 71b is disposed between the light detection unit 40 and the storage member 20; and the light blocking state Q2 (see FIG. 12) in which the light blocking portion 72 is disposed between the light detection unit 40 and the storage member 20.

The through-hole 71a penetrates the plate-shaped light adjuster 70 in the Z direction, and has an inner diameter that corresponds to the opening of the light detection unit 40 in a plan view. The light reducing filter portion 71b is fitted in a through-hole formed in the light adjuster 70, and allows part of the light incident thereto to be transmitted therethrough. The light reducing filter portion 71b is formed to have an outer diameter that corresponds to the opening of the light detection unit 40 in a plan view. When the light transmittance of the through-hole 71a is assumed to be 100%, the light reducing filter portion 71b has a light transmittance of about 3%, and the light blocking portion 72 has a light transmittance of about 0%, for example. In other words, the light blocking portion 72 blocks about 100% of light, the light reducing filter portion 71b blocks about 97% of light, and the through-hole 71a blocks 0% of light. The light blocking portion 72 is a shield plate composed of a portion of the plate-shaped light adjuster 70, with the light adjuster 70 being formed of a material that does not allow light to be transmitted therethrough. The light blocking portion 72 is larger than the opening of the light detection unit 40 in a plan view so that the light blocking portion 72 covers the light-receiving position 102 at least.

In the configuration example shown in FIG. 8 and FIG. 9, the reflector 60 is disposed so as to be opposed to the light adjuster 70 with the storage member 20 interposed therebetween. Specifically, the reflector 60 includes a first portion 62 opposed to the through-hole 71a of the light adjuster 70; and a second portion 63 opposed to the light reducing filter portion 71b. The first portion 62 is larger than the through-hole 71a so as to cover the through-hole 71a in a plan view. The second portion 63 is larger than the light reducing filter portion 71b so as to cover the light reducing filter portion 71b in a plan view. The reflector 60 is not provided at the position opposed to the light blocking portion 72.

Figure 11:
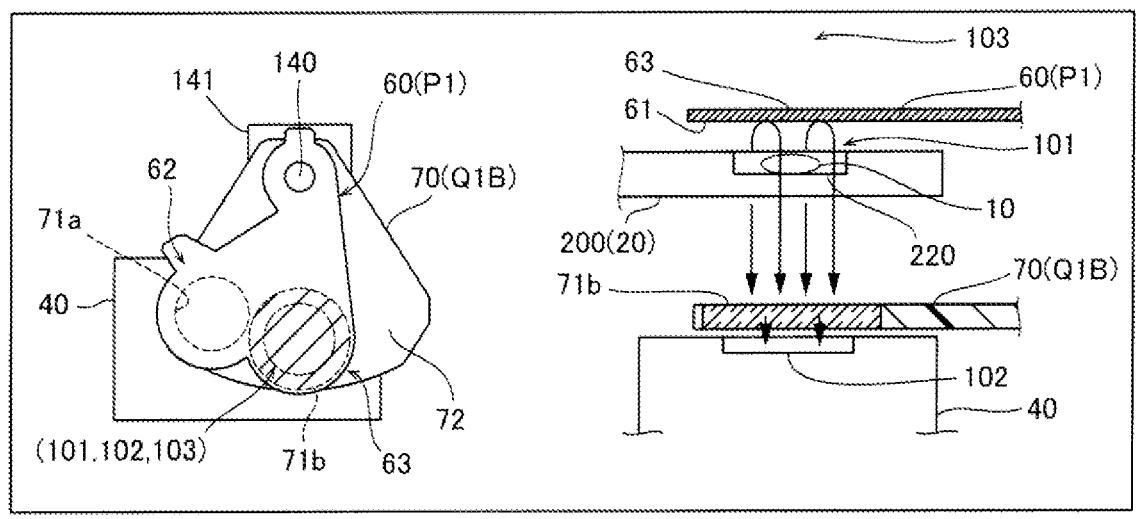
FIG. 11 is a schematic plan view and a schematic cross-sectional side view of the reflector and the light adjuster for describing the reflecting state and a second light transmitting state.
Figure 12:
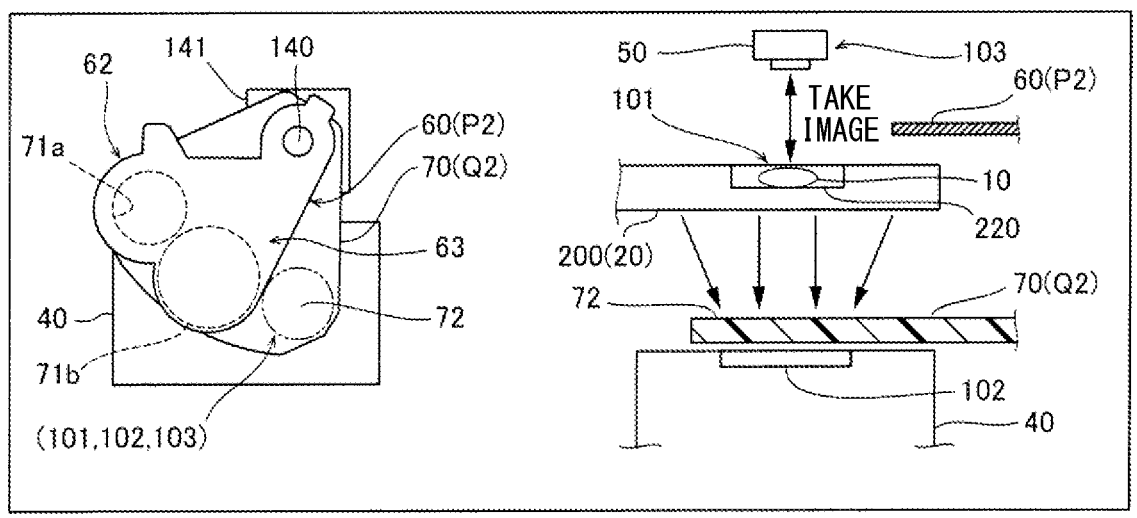
FIG. 12 is a schematic plan view and a schematic cross-sectional side view of the reflector and the light adjuster for describing the non-reflecting state and a light blocking state.

With this configuration, in the configuration example shown in FIG. 8 and FIG. 9, the reflector 60 is switched to be in the reflecting state P1 when the light adjuster 70 is in the light transmitting state Q1 (see FIG. 10, FIG. 11), and the light adjuster 70 is switched to be in the light blocking state Q2 when the reflector 60 is in the non-reflecting state P2 (see FIG. 12). With this configuration, when the light adjuster 70 is in the light transmitting state Q1, the reflector 60 in the reflecting state P1 reflects light from the sample 10, whereby the detection sensitivity can be enhanced. When the reflector 60 is in the non-reflecting state P2 (see FIG. 12), the light adjuster 70 enters the light blocking state Q2. Thus, while an image is taken by the imaging unit 50, light can be prevented from entering the light detection unit 40 and thus suppressed from affecting the detection sensitivity.

Figure 10:
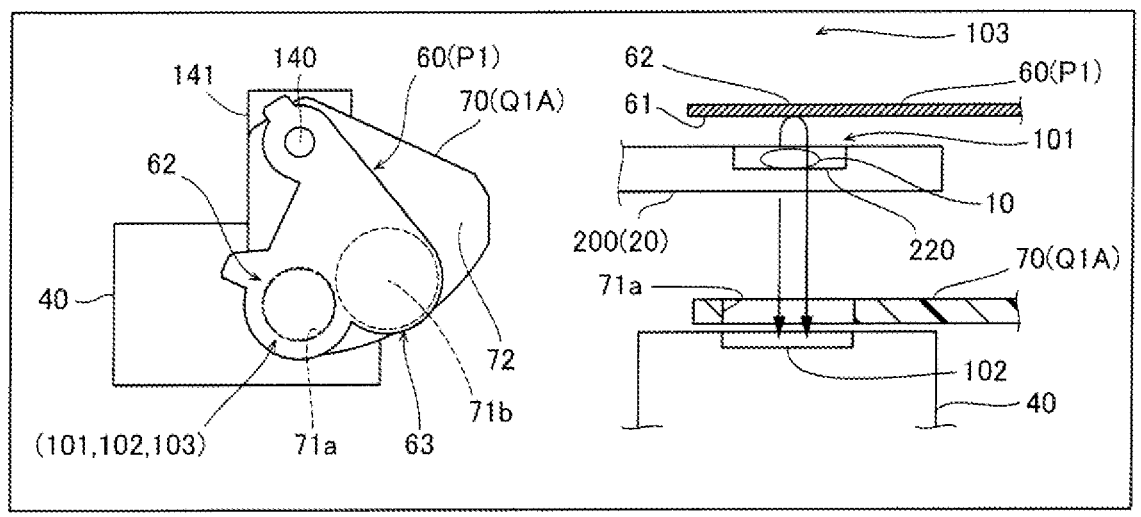
FIG. 10 is a schematic plan view and a schematic cross-sectional side view of the reflector and the light adjuster for describing the reflecting state and a first light transmitting state.

In FIG. 10 to FIG. 12, the reflector 60 is switched to the reflecting state P1 (see FIG. 10, FIG. 11) when light from the sample 10 is detected by the light detection unit 40, and the reflector 60 is switched to the non-reflecting state P2 (see FIG. 12) when light from the sample 10 is not detected by the light detection unit 40. The light adjuster 70 is switched to the light transmitting state Q1 (state Q1A in FIG. 10 or state Q1B in FIG. 11) when light from the sample 10 is detected by the light detection unit 40, and the light adjuster 70 is switched to the light blocking state Q2 (see FIG. 12) when light from the sample 10 is not detected by the light detection unit 40. Accordingly, when light detection is performed by the light detection unit 40, the detection sensitivity can be enhanced by causing light from the sample 10 to be reflected. Other than when the light detection is performed, an image of the sample 10 can be taken by the imaging unit 50 as necessary, while light is prevented from entering the light detection unit 40 and thus suppressed from affecting the detection sensitivity.

Description of Operation of Analyzer

Figure 13:
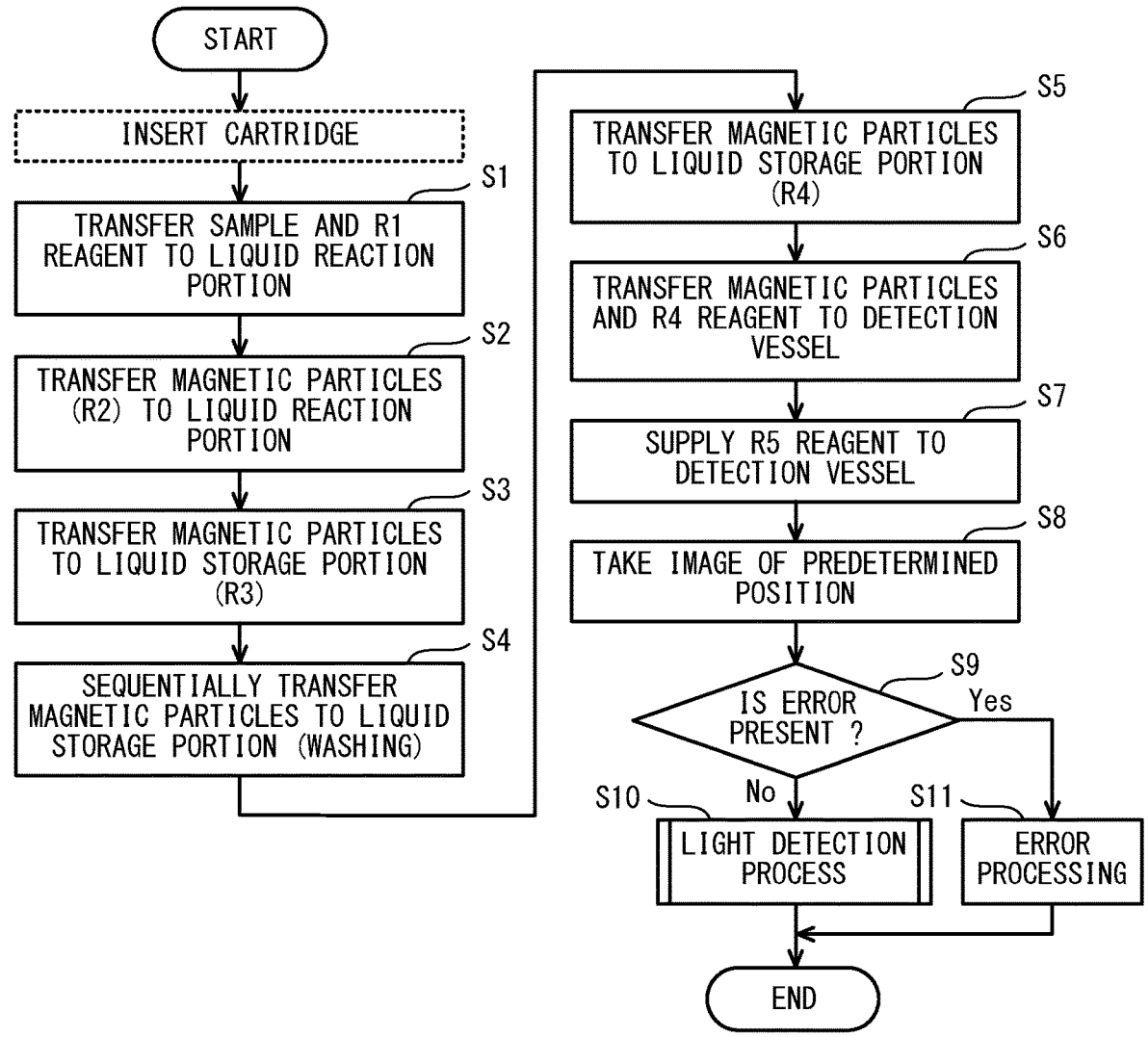
FIG. 13 is a flow chart for describing a measurement operation performed by the analyzer.

FIG. 13 shows an example of operation performed when a predetermined assay is conducted by use of the analyzer 100 and the cartridge 200 of the present embodiment. In the description of the operation, as to the configuration of the cartridge 200, FIG. 4 is referred to. As to the configuration of the analyzer 100, FIG. 5 to FIG. 7 are referred to. As to the states of the reflector 60 and the light adjuster 70, FIG. 10 to FIG. 12 are referred to. Control of the components of the analyzer 100 is performed by the controller 115.

At the start of measurement operation, the controller 115 causes the drive source 141 to rotate the rotation shaft 140 to a predetermined angle, thereby switching the light adjuster 70 to the light blocking state Q2 (see FIG. 12). The reflector 60 enters the non-reflecting state P2. Accordingly, also at the time of insertion of the cartridge 200, unnecessary light is suppressed from being incident on the light detection unit 40.

First, a user inserts the cartridge 200 into the slot of the analyzer 100. The cartridge 200 is taken out of a package, and a specimen collected from a patient is injected into the cartridge 200. Then, the cartridge 200 is inserted into the slot of the analyzer 100, thereby being held by the holder 30. The test substance in the specimen contains an antigen, for example. One example of the antigen is Hepatitis B surface antigen (HBsAg). The test substance may be one or more of antigens, antibodies, or other proteins.

When the cartridge 200 is set at the holder 30, taking images of the cartridge 200 by the imaging unit 50 is enabled. The controller 115 may turn on the lighting units 51 and may cause the imaging unit 50 to take images of phases of the measurement operation. Since the light adjuster 70 has been switched to the light blocking state Q2 (see FIG. 12), light from the lighting units 51 is suppressed from being incident on the light detection unit 40.

In step S1, the specimen is sent to the liquid reaction portion 230. The controller 115 controls the plunger unit 90 to push down the air chamber 261. The air sent out from the air chamber 261 causes the specimen to flow through the passage portion 250 together with an R1 reagent stored in the liquid storage portion 211, to be pushed into the liquid reaction portion 230. In a case where the imaging unit 50 takes images of the liquid reaction portion 230, whether the specimen and the R1 reagent have reached the liquid reaction portion 230 can be determined on the basis of the taken images.

The R1 reagent contains a capture substance that binds to the test substance. The capture substance contains an antibody that binds to the test substance, for example. The antibody is a biotin-bound HBs monoclonal antibody, for example. The test substance and the R1 reagent bind to each other through antigen-antibody reaction.

In step S2, the analyzer 100 transfers, to the liquid reaction portion 230, magnetic particles contained in an R2 reagent stored in the liquid storage portion 212. The magnetic particles are dispersed in the liquid component of the R2 reagent. The controller 115 causes the magnet unit 80 to move, thereby to collect magnetic particles in the liquid storage portion 212 by the magnetic force of the magnet 81a and move the collected magnetic particles to the liquid reaction portion 230. In a case where the imaging unit 50 takes images of the liquid reaction portion 230, whether the magnetic particles have reached the liquid reaction portion 230 can be determined on the basis of the taken images.

In the liquid reaction portion 230, a magnetic-particle-bound body is generated through reaction between the magnetic particles and the antigen-antibody reaction product. That is, the test substance bound to the capture substance in the R1 reagent binds to magnetic particles via the capture substance. The magnetic particles serve as the carrier for the test substance. The magnetic particles are, for example, streptavidin-bound magnetic particles, the surfaces of which are coated with avidin.

In step S3, the analyzer 100 transfers, by the magnetic force of the magnet 81a, the magnetic-particle-bound body to the liquid storage portion 213 storing an R3 reagent therein. In a case where the imaging unit 50 takes images of the liquid storage portion 213, whether the magnetic-particle-bound body has reached the liquid storage portion 213 can be determined on the bases of the taken images.

The R3 reagent contains a labeled substance. The labeled substance contains a labeled antibody, for example. The labeled antibody is an ALP labeled HBsAg monoclonal antibody, for example. The labeled antibody contained in the R3 reagent and the magnetic-particle-bound body are allowed to react with each other. Through the reaction between the magnetic-particle-bound body and the labeled antibody, an immune complex is generated. The immune complex contains the test substance, the capture antibody, the labeled antibody and the magnetic particles.

In step S4, the analyzer 100 sequentially transfers the immune complex to the liquid storage portions 214 to 216 by the magnetic force of the magnet 81a. Each of the liquid storage portions 214 to 216 stores a washing liquid. The controller 115 causes the immune complex and unreacted substances to be separated from each other in the liquid storage portions 214 to 216, three times in total. That is, unreacted substances are removed through washing. In a case where the imaging unit 50 takes images of the liquid storage portions 214 to 216, whether the immune complex has reached to each of the liquid storage portions 214 to 216 can be determined on the basis of the taken images.

The controller 115 causes the magnet unit 80 to be moved in the up-down direction at each of liquid storage portions 214 to 216 so as to cause the magnet 81a and the magnet 81b to alternately approach the immune complex, thereby stirring the immune complex in the washing liquid in each of the liquid storage portions 214 to 216. As a result, unreacted substances are separated from the immune complex.

In step S5, the analyzer 100 transfers the immune complex to the liquid storage portion 217 by the magnetic force of the magnet 81a. In a case where the imaging unit 50 takes images of the liquid storage portion 217, whether the washed immune complex has reached the liquid storage portion 217 can be determined on the bases of the taken images.

The liquid storage portion 217 stores an R4 reagent therein. The R4 reagent has a composition that promotes luminescence of the immune complex. The R4 reagent is a buffer solution, for example. The immune complex reacts, in the liquid storage portion 217, with the buffer solution contained in the R4 reagent.

In step S6, the analyzer 100 transfers, to the detection vessel 220, the mixture of the immune complex and the buffer solution. The controller 115 controls the plunger unit 90 to push down the air chamber 262, to push out the mixture of the immune complex and the buffer solution through the passage portion 250 into the detection vessel 220. In a case where the imaging unit 50 takes images of the detection vessel 220, whether the mixture of the immune complex and the buffer solution has reached the detection vessel 220 can be determined on the basis of the taken images.

In step S7, the analyzer 100 transfers an R5 reagent stored in the liquid storage portion 218 to the detection vessel 220. The controller 115 controls the plunger unit 90 to push down the air chamber 263, to push out the R5 reagent from the liquid storage portion 218 into the detection vessel 220. In a case where the imaging unit 50 takes images of the detection vessel 220, whether the R5 reagent has reached the detection vessel 220 can be determined on the basis of the taken images.

The R5 reagent contains, for example, a substrate that reacts with the immune complex to promote luminescence. The R5 reagent is added to the mixture of the immune complex and the buffer solution in the detection vessel 220. The luminescent substrate and the immune complex react with each other. As a result, a sample 10 that generates light is prepared in the detection vessel 220.

In step S8, the controller 115 causes the imaging unit 50 to take an image of the sample 10 in a state where the reflector 60 is switched at the non-reflecting state P2. In step S9, the controller 115 determines whether an error is present with respect to the state of the sample 10 on the basis of the taken image. When no error is present, then, in step S10, the analyzer 100 performs a light detection process. When an error is present, the controller 115 does not perform the subsequent detection processing operation, but causes the display part 112 and the indicator 113 to display the error in step S11. In this manner, on the basis of the taken image of the sample 10, the controller 115 controls the light detecting operation that uses the light detection unit 40. Thus, whether the sample 10 is present in the detection vessel 220 and whether the state of the sample 10 is appropriate can be determined on the basis of the taken image. As a result, in such a case where the state of the sample 10 is not appropriate, it is possible to stop the process without performing the light detecting operation and quickly notify the user, and to correct the analysis result in accordance with the state of the sample 10.

Figure 18A:
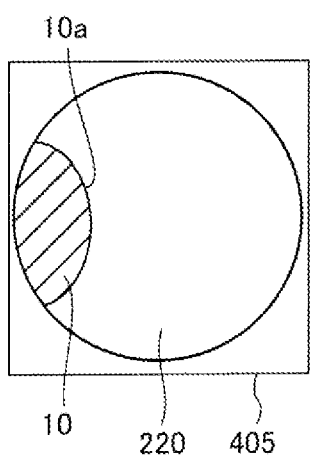
FIG. 18A is a schematic diagram for describing a liquid sending error determination based on a taken image.

In the error determination based on the taken image, the controller 115 determines whether the sample 10 has normally reached the detection vessel 220 on the basis of the shape of the sample 10 in a taken image 405, as shown in FIG. 18A, for example. The shape of the sample 10 is obtained by detecting a contour 10*a* of the liquid portion where the sample 10 is present in the detection vessel 220 in the taken image 405. The contour 10*a* of the liquid portion can be detected through a known edge detection technique. For example, when the area of the region surrounded by the contour 10*a* of the sample 10 relative to the area of the detection vessel 220 is smaller than an allowable range, the controller 115 determines that a liquid sending error is present. Thus, the liquid sending error indicates that the sample 10 has not normally reached the detection vessel 220. When the area of the sample 10 is within the allowable range, the controller 115 determines that the liquid sending of the sample 10 is normal.

Figure 18B:
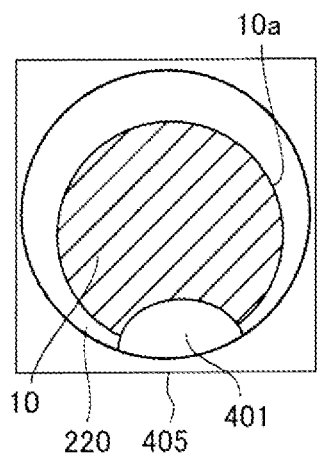
FIG. 18B is a schematic diagram for describing a bubble-mixture error determination based on a taken image.

As shown in FIG. 18B, for example, the controller 115 determines whether a bubble has been mixed into the detection vessel 220, on the basis of the shape of the sample 10 in the taken image 405. The controller 115 determines, through edge detection, whether a bubble portion 401 is present between the detection vessel 220 and the sample 10. For example, when the area of the bubble portion 401 is larger than an allowable range, the controller 115 determines that a bubble-mixture error is present. When the bubble portion 401 is not detected, or when the area of the bubble portion 401 is in the allowable range, the controller 115 determines that the bubble mixture state is normal.

Figure 18C:
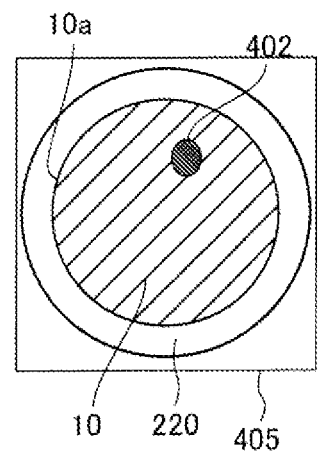
FIG. 18C is a schematic diagram for describing a magnetic particles aggregation error determination based on a taken image.

As shown in FIG. 18C, for example, the controller 115 determines whether an aggregation region 402 of magnetic particles is present in the taken image 405. Magnetic particles each have a very small particle size, and thus are not recognized in an image when the magnetic particles are in a normally dispersed state. However, when the magnetic particles are aggregated, the magnetic particles are recognized in the image as an opaque colored region, accordingly. The controller 115 determines whether the aggregation region 402 in which the magnetic particles have been aggregated is present inside the sample 10, on the basis of change in color or in contrast inside the contour 10*a* of sample 10. When the aggregation region 402 is present inside the contour 10*a* of the sample 10, the controller 115 determines that an aggregation error of the magnetic particles is present. When the aggregation region 402 is not detected, the controller 115 determines that the presence/absence of the aggregation is normal.

It should be noted that even when an error has been detected with respect to the state of the sample 10 on the basis of the taken image 405, the controller 115 may perform the subsequent detection processing operation (step S10), for example, but may cause the display part 112 to display an indication of a possible error together with an analysis result.

When none of the errors has been detected in step S9, then, in step S10, the analyzer 100 performs a light detection process. That is, the controller 115 causes the light detection unit 40 to detect light that has been generated through reaction between the luminescent substrate and the labeled antibody of the immune complex. When any of the errors has been detected, then, in step S11, the controller 115 causes the display part 112 and the indicator 113 to display predetermined error information in accordance with the type of the error determined in step S9.

Next, details of the light detection process using the light detection unit 40 and performed in step S10 are described.

Figure 14:
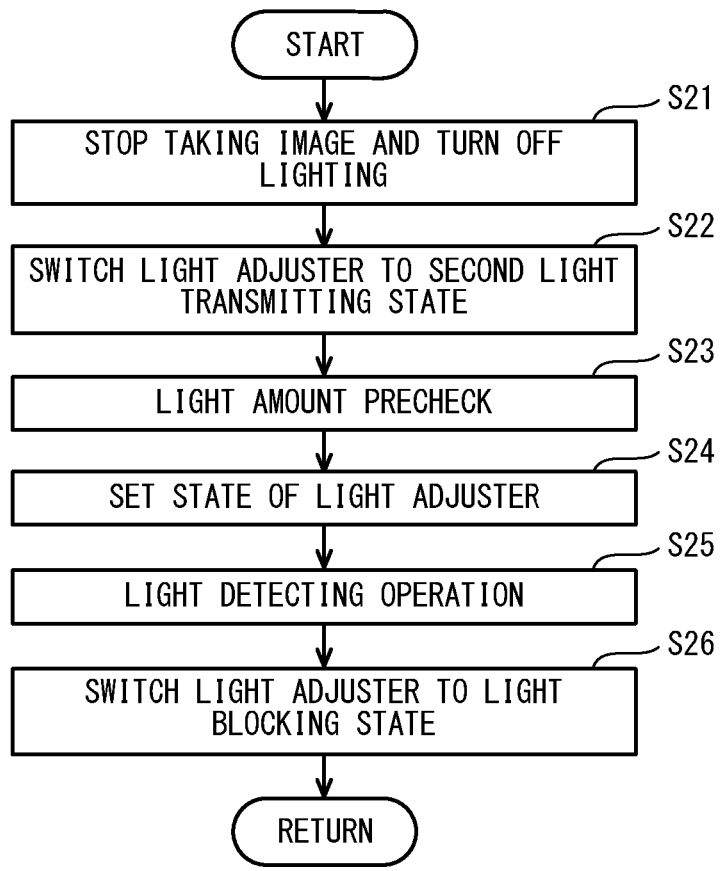
FIG. 14 is a flow chart for describing a light detection process performed by the analyzer.

In step S21 in FIG. 14, the controller 115 turns off the lighting units 51, to stop taking images performed by the imaging unit 50.

In step S22, the controller 115 controls the drive source 141 to rotate the rotation shaft 140 by a predetermined angle, thereby switching the light adjuster 70 to the second light transmitting state Q1B. The reflector 60 is switched to the reflecting state P1, with the second portion 63 set accordingly.

In step S23, the controller 115 prechecks a detection light amount by use of the light detection unit 40. That is, in a state where the reflector 60 is switched at the reflecting state P1 and the light adjuster 70 is switched at the second light transmitting state Q1B, light detection is performed once.

In step S24, the controller 115 sets a state of the light adjuster 70. For example, when the detection light amount obtained at the precheck is not lower than a predetermined threshold, the controller 115 sets the light adjuster 70 to the second light transmitting state Q1B. In this case, the reflector 60 and the light adjuster 70 are kept in the states thereof at the precheck. For example, when the detection light amount at the precheck is less than the predetermined threshold, the controller 115 controls the drive source 141 to rotate the rotation shaft 140 by a predetermined angle, thereby switching the light adjuster 70 to the first light transmitting state Q1A. That is, in order to set the light adjuster 70 to the first light transmitting state Q1A, the controller 115 sets the rotation angle of the rotation shaft 140 to a predetermined value. The reflector 60 is kept at the reflecting state P1, with the first portion 62 set accordingly. As a result of the precheck, saturation of the detection signal of the light detection unit 40 can be avoided, and light detection at an appropriate sensitivity can be realized.

In step S25, the controller 115 causes the light detection unit 40 to perform light detection. For example, the light detection unit 40 counts the number of photons incident on the light-receiving position 102, and outputs the detection result to the analysis unit 116. The analysis unit 116 outputs an analysis result of the sample 10 on the basis of the light amount detected by the light detection unit 40. For example, the analysis unit 116 compares the detection value of the detected number of photons with a standard curve, thereby determining the presence/absence of the test substance or quantitatively determining the concentration or the like of the test substance.

As described above, the controller 115 controls the light detection unit 40 so as to detect light from the sample 10 in a state where the reflector 60 has been switched to the reflecting state P1 after an image of the sample 10 had been taken. The analysis unit 116 outputs an analysis result of the sample 10 on the basis of the light amount detected by the light detection unit 40 in the reflecting state P1. Thus, an analysis result having a higher accuracy is obtained on the basis of the light amount detected at a higher sensitivity which is realized by the reflected light from the reflector 60 also being detected.

When the light detection is completed, then, in step S26, the controller 115 controls the drive source 141 to rotate the rotation shaft 140 by a predetermined angle, thereby switching the light adjuster 70 to the light blocking state Q2. At this time, the reflector 60 is switched to the non-reflecting state P2. As a result, also when the cartridge 200 whose analysis has been ended is to be taken out, unnecessary light is suppressed from being incident on the light detection unit 40.

In this manner, the measurement operation using the cartridge 200 is performed by the analyzer 100.

Other Configuration Examples of Analyzer

Next, with reference to FIG. 15 to FIG. 17, other configuration examples of the analyzer are described.

Figure 15A:
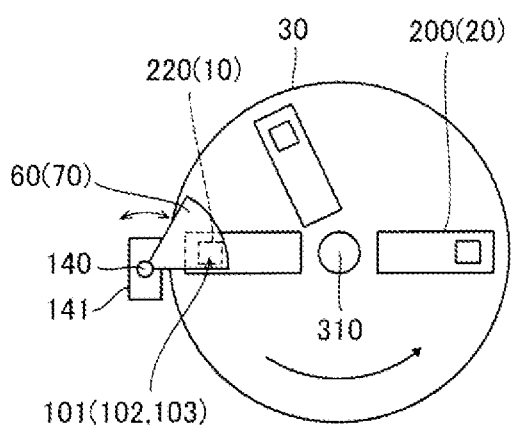
FIG. 15A is a schematic diagram showing another configuration example of the holder of the analyzer.

In the configuration example shown in FIG. 15, the holder 30 can move the storage member 20 in a state where the holder 30 holds the storage member 20. FIG. 15A is a schematic diagram of the holder 30 in a plan view. The holder 30 is formed in a disk shape and can be rotated about a rotation shaft 310 at the center by a drive source not shown. Thus, the holder 30 moves the storage member 20 placed on the holder 30 to the predetermined position 101. The holder 30 can hold a plurality of the storage members 20 and sequentially moves the storage members 20 placed thereon to the predetermined position 101. This allows light detection to be continuously performed on the plurality of the storage members 20. At the predetermined position 101, the reflector 60 and the light adjuster 70 are disposed.

Figure 15B:
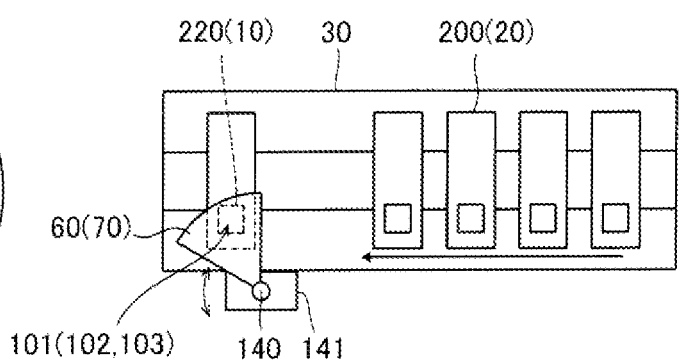
FIG. 15B is a schematic diagram showing another configuration example of the holder of the analyzer.

In the configuration example shown in FIG. 15B, the holder 30 can linearly move the storage member 20 in a state where the holder 30 holds the storage member 20. FIG. 15B is a schematic diagram of the holder 30 in a plan view. The holder 30 includes, for example, a belt conveyer, a linear motion mechanism, and the like, and can transfer the storage member 20 placed at a placement position to the predetermined position 101. The holder 30 can hold a plurality of the storage members 20, and sequentially moves the storage members 20 placed thereon to the predetermined position 101. At the predetermined position 101, the reflector 60 and the light adjuster 70 are disposed.

FIG. 16 shows other configuration examples of the reflector 60 or the light adjuster 70. Although FIG. 8 shows an example in which the reflector 60 and the light adjuster 70 are each formed in a substantially fan shape, the reflector 60 may be formed in a rectangular plate shape as shown in FIG. 16A. As shown in FIG. 16B, the light adjuster 70 may include the light transmitting portion 71 and the light blocking portion 72 each in a rectangular shape. The reflector 60 and the light adjuster 70 may each have any shape.

Figure 16A:
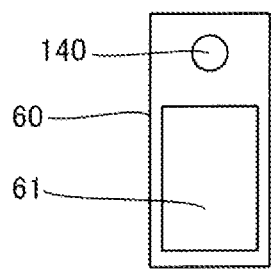
FIG. 16A is a schematic diagram showing another configuration example of the reflector and the light adjuster of the analyzer.
Figure 16B:
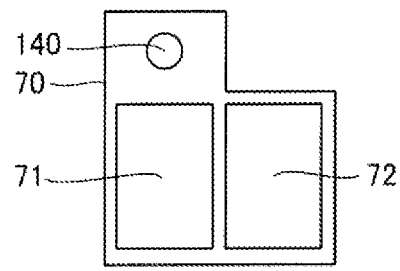
FIG. 16B is a schematic diagram showing another configuration example of the reflector and the light adjuster of the analyzer.
Figure 16C:
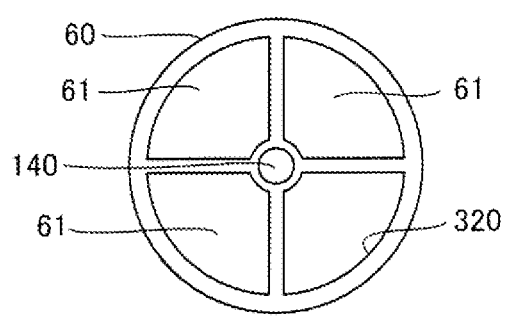
FIG. 16C is a schematic diagram showing another configuration example of the reflector and the light adjuster of the analyzer.
Figure 16D:
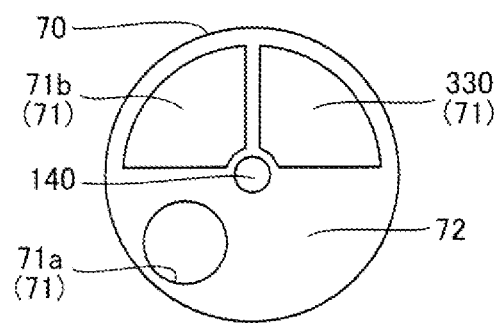
FIG. 16D is a schematic diagram showing another configuration example of the reflector and the light adjuster of the analyzer.

In the configuration examples shown in FIGS. 16C and 16D, the reflector 60 and the light adjuster 70 each have a disk shape. FIGS. 16C and 16D are schematic diagrams of the reflector 60 and the light adjuster 70 in plan views, respectively. As shown in FIG. 16C, for example, the reflector 60 may include a portion in which the reflection face 61 is formed, and a portion in which a through-hole 320 is formed. The reflector 60 enters the non-reflecting state P2 by the through-hole 320 being located between the storage member 20 and the imaging unit 50.

As shown in FIG. 16D, for example, the light adjuster 70 may include a filter portion other than the light reducing filter portion 71b and the through-hole 71a. For example, the light adjuster 70 may include a wavelength filter portion 330 provided with an optical bandpass filter that allows only light having a predetermined wavelength to be transmitted therethrough. The shapes of the through-hole 71a, the light blocking portion 72, and the filter portion are not limited in particular. As shown in FIG. 16D, as the shape of the filter portion, a fan shape, a circular shape, or any shape other than these may be employed.

Figure 17A:
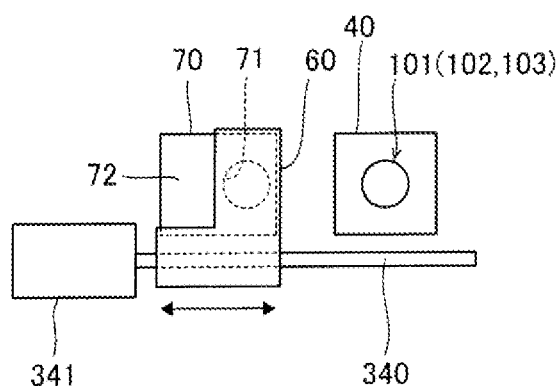
FIG. 17A is a schematic diagram showing another configuration example for moving the reflector and the light adjuster of the analyzer.

In the configuration example shown in FIG. 17A, the reflector 60 and the light adjuster 70 can linearly move in the horizontal direction. FIG. 17A is a schematic diagram showing the reflector 60 and the light adjuster 70, and the light detection unit 40, in a plan view. The reflector 60 and the light adjuster 70 are disposed at upper positions relative to the light detection unit 40 and are provided such that the reflector 60 and the light adjuster 70 overlap with each other in the up-down direction. The reflector 60 and the light adjuster 70 are mounted to a shaft 340 linearly extending in the horizontal direction, and are linearly moved in the horizontal direction by a drive source 341. Accordingly, by linearly moving in the horizontal direction, the reflector 60 enters the reflecting state P1 at a reflecting position opposed to the light detection unit 40 with the storage member 20 at the predetermined position 101 interposed therebetween, and enters the non-reflecting state P2 at a withdrawn position where the reflector 60 does not block the space between the imaging unit 50 and the storage member 20 at the predetermined position 101. Similarly, by linearly moving in the horizontal direction, the light adjuster 70 is switched between the light transmitting state Q1 in which the light transmitting portion 71 is disposed between the light detection unit 40 and the storage member 20 at the predetermined position 101; and the light blocking state Q2 in which the light blocking portion 72 is disposed between the light detection unit 40 and the storage member 20 at the predetermined position 101.

Figure 17B:
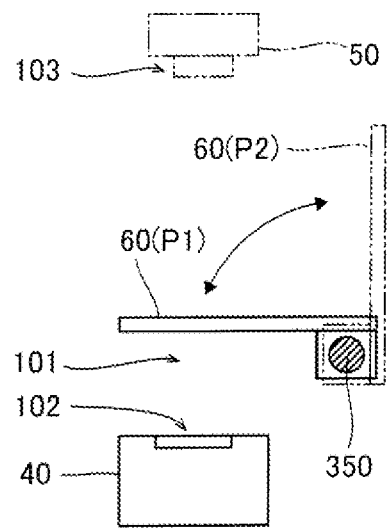
FIG. 17B is a schematic diagram showing another configuration example for moving the reflector and the light adjuster of the analyzer.

In the configuration example shown in FIG. 17B, the reflector 60 can rotate toward the up-down direction about a rotation shaft 350 extending in the horizontal direction. FIG. 17B is a schematic side view showing the reflector 60 and the light detection unit 40, viewed from the direction in which the rotation shaft 350 extends. The reflector 60 rotates about the rotation shaft 350 to enter a substantially horizontal state, thereby being disposed at a reflecting position opposed to the light detection unit 40 with the storage member 20 at the predetermined position 101 interposed therebetween, whereby the reflector 60 enters the reflecting state P1. The reflector 60 rotates about the rotation shaft 350 to enter a substantially perpendicular state, thereby being disposed at a withdrawn position at which the reflector 60 does not block the space between the imaging unit 50 and the storage member 20 at the predetermined position 101, whereby the reflector 60 enters the non-reflecting state P2.

The light adjuster 70 can be configured similarly to the light reflector 60 shown in FIG. 17B. The light adjuster 70 enters a substantially perpendicular state, thereby entering the light transmitting state in which light advancing from the storage member 20 at the predetermined position 101 toward the light detection unit 40 is allowed to be transmitted therethrough. The light adjuster 70 enters a substantially horizontal state, thereby entering the light blocking state in which light advancing from the storage member 20 at the predetermined position 101 toward the light detection unit 40 is blocked.

It should be noted that the embodiments disclosed herein are merely illustrative in all aspects and should not be considered as restrictive. The scope of the present disclosure is defined not by the description of the above embodiments but by the scope of the claims, and includes meaning equivalent to the scope of the claims and all changes within the scope.

What is claimed is:

1. An analyzer comprising:
a holding device comprising at least one support surface, the at least one support surface configured to support a storage container such that the holding device is configured to hold the storage container at a first location between a light sensor and an imaging unit, the storage container storing therein a sample prepared so as to emit light in accordance with an amount of a test substance;
the light sensor oriented in a first direction facing the first location between the light sensor and the imaging unit and configured to detect light from the sample stored in the storage container held by the holding device;
the imaging unit oriented in a second direction facing the first location between the light sensor and the imaging unit, the second direction being opposite the first direction, the imaging unit configured to take an image of the storage container;
a mirror mechanically coupled with an actuator so as to be switchably placed at a first position in which the mirror is placed between the first location and the imaging unit, wherein the mirror is configured to reflect light from the sample in the storage container that originally advances toward the imaging unit toward the light sensor when in the first position, and a second position, wherein the mirror is configured to allow the light that originally advances toward the imaging unit to pass unhindered by the mirror to the imaging unit when in the second position; and
a controller programmed to cause the light sensor to detect light emitted from the test substance in the storage container while controlling the actuator to place the mirror at the first position, and to cause the imaging unit to take an image of the storage container while controlling the actuator to place the mirror at the second position.

2. The analyzer of claim 1, wherein the holding device is configured to detachably hold a cartridge-type storage container in which the sample is prepared by receiving a test substance and by allowing the test substance to bind to a labeled substance, the holding device being configured to be disposed at a predetermined position at which the imaging unit is allowed to take an image of a detection vessel which is in the storage container and which has stored therein the sample.

3. The analyzer of claim 1, further comprising:
a processing unit configured to perform analysis on the basis of a light amount detected by the light sensor, wherein
the controller is programmed to control the light sensor so as to detect light from the sample in a state where the mirror is switched to the first position after the image of the sample has been taken, and
the processing unit outputs an analysis result of the sample on the basis of a light amount detected by the light sensor when the mirror is in the first position.

4. The analyzer of claim 1, wherein the controller is further programmed to digitally analyze the image of the storage container to determine that an error with respect to the sample in the storage container exists.

5. The analyzer of claim 1, wherein the controller is programmed to cause the actuator to place the mirror at the second position to take the image of the storage container and determine whether an error with respect to the sample in the storage container exists, and then cause the actuator to place the mirror at the first position to detect the light from the storage container by the light sensor.

6. The analyzer of claim 5, wherein the controller is programmed to terminate an analysis sequence without detecting the light from the storage container by the light sensor in response to determining that the error exists.

7. The analyzer of claim 5, wherein the controller is programmed to provide a notification regarding the error in response to determining that the error exists.

8. The analyzer of claim 1, further comprising a plunger unit operatively disposed in relation to the first location and configured to transport a test substance in the sample within the storage container to a detection vessel, and the controller is programmed to determine whether the test substance has properly been transported to the detection vessel, on the basis of the image of the storage container.

9. The analyzer of claim 8, wherein the controller is programmed to determine whether a bubble is present in the image of the detection vessel.

10. The analyzer of claim 8, wherein the controller is programmed to determine whether aggregated magnetic particles are present in the image of the detection vessel.

11. The analyzer of claim 1, further comprising a light adjuster, disposed between the light sensor and the storage container held by the holding device, comprising a plate member having a first portion configured to allow light from the storage container to be transmitted and a second portion configured to block the light, wherein the plate member is movable under control of the controller.

12. The analyzer of claim 11, wherein the mirror and the light adjuster are coupled to the actuator and moved in conjunction with each other.

13. The analyzer of claim 11, further comprising a light adjuster, disposed between the light sensor and the storage container held by the holding device, comprising a plate member having a first portion configured to allow light from the storage container to be transmitted, a second portion configured to block the light, and a third portion configured to partially block the light.

14. An analyzer comprising:
a shaft configured to rotate about an axis of the shaft and further comprising a holder configured to support a storage container at a first location between a light sensor and an imaging unit and wherein the shaft is configured to rotate the holder and the storage container about the axis of the shaft, the storage container storing therein a sample prepared so as to emit light in accordance with an amount of a test substance;
the light sensor positioned offset from the axis of the shaft and oriented in a first direction facing the first location between the light sensor and the imaging unit and configured to detect light from the sample stored in the storage container supported by the shaft;
the imaging unit positioned offset from the axis of the shaft and oriented in a second direction facing the first location between the light sensor and the imaging unit, the second direction being opposite the first direction, the imaging unit configured to take an image of the storage container;
a mirror mechanically coupled with an actuator so as to be switchably placed at a first position in which the mirror is placed between the first location and the imaging unit, wherein the mirror is configured to reflect light from the sample in the storage container that originally advances toward the imaging unit toward the light sensor when in the first position, and a second position, wherein the mirror is configured to allow the light that originally advances toward the imaging unit to pass unhindered by the mirror to the imaging unit when in the second position; and
a controller programmed to cause the light sensor to detect light emitted from the test substance in the storage container while controlling the actuator to place the mirror at the first position, and to cause the imaging unit to take an image of the storage container while controlling the actuator to place the mirror at the second position.

15. The analyzer of claim 14, wherein the holder is configured to detachably hold a cartridge-type storage container in which the sample is prepared by receiving a test substance and by allowing the test substance to bind to a labeled substance, the shaft configured to dispose a detection vessel of the storage container, in which the sample is stored, at a predetermined position at which the imaging unit can take an image of the detection vessel.

16. The analyzer of claim 14, further comprising:
a processing unit configured to perform analysis on the basis of a light amount detected by the light sensor, wherein
the controller is programmed to control the light sensor so as to detect light from the sample in a state where the mirror is switched to the first position after the image of the sample has been taken, and
the processing unit outputs an analysis result of the sample on the basis of a light amount detected by the light sensor when the mirror is in the first position.

17. The analyzer of claim 14, wherein the controller is further programmed to digitally analyze the image of the storage container to determine that an error with respect to the sample in the storage container exists.

18. The analyzer of claim 17 wherein the controller is programmed to determine whether at least one of a bubble is present in the image of the detection vessel or aggregated magnetic particles are present in the image of the detection vessel.

19. The analyzer of claim 14, further comprising a plunger unit operatively disposed in relation to the first location and configured to transport a test substance in the sample within the storage container to a detection vessel, and the controller is programmed to determine whether the test substance has properly been transported to the detection vessel on the basis of the image of the storage container.

20. The analyzer of claim 14, further comprising a light adjuster, disposed between the light sensor and the storage container, comprising a plate member having a first portion configured to allow light from the storage container to be transmitted and a second portion configured to block the light, wherein the plate member is movable under control of the controller.

* * * * *